(12) United States Patent
Faham et al.

(10) Patent No.: US 7,208,295 B2
(45) Date of Patent: Apr. 24, 2007

(54) MULTIPLEX OLIGONUCLEOTIDE ADDITION AND TARGET AMPLIFICATION

(75) Inventors: Malek Faham, Pacifica, CA (US); Jianbiao Zheng, Mountain View, CA (US)

(73) Assignee: Affymetrix, Inc., Santa Clara, CA (US)

( * ) Notice: Subject to any disclaimer, the term of this patent is extended or adjusted under 35 U.S.C. 154(b) by 454 days.

(21) Appl. No.: 10/300,311

(22) Filed: Nov. 19, 2002

(65) Prior Publication Data

US 2003/0096291 A1  May 22, 2003

Related U.S. Application Data

(60) Provisional application No. 60/331,693, filed on Nov. 19, 2001.

(51) Int. Cl.
C12P 19/34 (2006.01)

(52) U.S. Cl. ..................... 435/91.1; 435/91.2

(58) Field of Classification Search ............... 436/6; 536/23.1, 24.3
See application file for complete search history.

(56) References Cited

U.S. PATENT DOCUMENTS

| | | | |
|---|---|---|---|
| 4,945,051 A * | 7/1990 | Kikuchi et al. ............. 435/206 |
| 5,185,243 A | 2/1993 | Ullman et al. ................. 435/6 |
| 5,439,793 A | 8/1995 | Rose et al. ................ 435/91.2 |
| 5,491,063 A | 2/1996 | Fisher et al. |
| 5,508,178 A | 4/1996 | Rose et al. ................ 435/91.1 |
| 5,525,494 A | 6/1996 | Newton |
| 5,565,340 A | 10/1996 | Chenchik .................. 435/91.2 |
| 5,582,989 A | 12/1996 | Caskey et al. |
| 5,595,891 A | 1/1997 | Rose et al. ................ 435/91.5 |
| 5,612,199 A | 3/1997 | Western et al. ........... 435/91.5 |
| 5,728,526 A | 3/1998 | George, Jr. et al. |
| 5,731,171 A | 3/1998 | Bohlander |
| 5,851,770 A | 12/1998 | Babon et al. .................. 435/6 |
| 5,882,856 A | 3/1999 | Shuber |
| 5,888,731 A | 3/1999 | Yager et al. |
| 5,928,905 A | 7/1999 | Stemmer et al. |
| 5,952,176 A | 9/1999 | McCarthy et al. ............. 435/6 |
| 6,045,994 A * | 4/2000 | Zabeau et al. ................. 435/6 |
| 6,117,679 A | 9/2000 | Stemmer ....................... 435/6 |
| 6,130,073 A | 10/2000 | Eggerding |
| 6,150,516 A | 11/2000 | Brenner et al. |
| 6,207,372 B1 | 3/2001 | Shuber |
| 6,207,424 B1 | 3/2001 | Chou et al. |
| 6,326,145 B1 | 12/2001 | Whitcombe et al. |
| 6,350,580 B1 | 2/2002 | Sorge |
| 6,355,422 B1 | 3/2002 | Liu et al. |
| 6,361,942 B1 | 3/2002 | Coull et al. |
| 6,410,278 B1 | 6/2002 | Notomi et al. ............. 435/91.2 |
| 2001/0049125 A1 | 12/2001 | Stemmer et al. |
| 2002/0102591 A1 | 8/2002 | Sorge |
| 2002/0119448 A1 | 8/2002 | Sorge et al. |
| 2002/0137036 A1 | 9/2002 | Sorge et al. |
| 2003/0104459 A1 | 6/2003 | Faham et al. |
| 2004/0224352 A1 * | 11/2004 | Fan et al. ....................... 435/6 |

FOREIGN PATENT DOCUMENTS

| | | |
|---|---|---|
| EP | 0 799 897 | 10/1997 |
| EP | 0971 039 A | 1/2000 |
| EP | 1020 534 A1 | 5/2000 |
| WO | WO 96/33207 | 10/1996 |
| WO | WO 96/41012 | 12/1996 |
| WO | WO 97/45559 | 12/1997 |
| WO | WO 99/49293 | 9/1999 |
| WO | WO-99/66071 | 12/1999 |
| WO | WO 01/06012 A1 | 1/2001 |
| WO | WO 01/32922 | 5/2001 |
| WO | WO 01/38556 | 5/2001 |
| WO | WO 01/94625 | 12/2001 |
| WO | WO 02/29112 | 4/2002 |
| WO | WO 02/36821 | 5/2002 |
| WO | WO 02/59354 | 8/2002 |
| WO | WO 02/59355 | 8/2002 |
| WO | WO 02/70751 | 9/2002 |

OTHER PUBLICATIONS

Eurogenetic, *Quantitative and Qualitative PCR Technology: All Types of Probes and Related Expertise in One Company*: pp. 1-47 (2002).
http://www4.amershambiosciences.com/aptrix/upp01077.nsf/Content/gel_blot_fluor_imaging.html "Multiplex PCR Product Analysis: Increased Accuracy and Throughput." (Oct. 31, 2002).
http://www.bu.edu/research/Features/sciocoalition_01/twist.html "A New Twist on a Powerful Theme." (Oct. 31, 2002).

(Continued)

*Primary Examiner*—James Martinell
(74) *Attorney, Agent, or Firm*—Sandra E. Wells; Ropes and Gray LLP

(57) ABSTRACT

Methods for appending oligonucleotides directly to nucleic acid templates, particularly to defined sites internal to single-stranded templates, are described. Appending first and second common priming sites to each of a plurality of templates of distinct sequence allows the subsequent stoichiometric amplification of a plurality of templates of distinct sequence.

29 Claims, 10 Drawing Sheets

OTHER PUBLICATIONS http://www.bu.edu/research/Features/sciocoalition_01/twist2.html "Return to a New Twist." (Oct. 31, 2002).

http://www.dxsgenotyping.com/technology_main.htm "Sorpions™ Technology for PCR Analysis." (Oct. 31, 2002).

http://www.eurogentec.be/code/en/thec_real_scor.htm "Scorpions™ Genomics Oligonucleotides Synthesis." (Oct. 31, 2002).

http://www.info.med.yale.edu/genetics/ward/tavi/Guide.html "PCR and Multiplex PCR Guide." (Oct. 31, 2002).

http://www.info.med.yale.edu/genetics/ward/tavi/p01.html "PCR Generalities." (Oct. 31, 2002).

http://www.info.med.yale.edu/genetics/ward/tavi/p02.html "Choosing/Designing PCR Primers." (Oct. 31, 2002.

http://www.info.med.yale.edu/genetics/ward/tavi/p04.html "Multiplexing Primer Pairs." (Oct. 31, 2002).

http://www.mdlab.com/fees&servs/serv-polymerase.html "Medical Diagnostic Laboratories Diagnostic Services: Application of the Polymerase Chain Methodologies in Molecular Diagnostic Medicine." (Oct. 31,, 2002).

http://www.medprobe.com/no/rtper.html "MedProbe: Real Time PCR Products and Instruments." (Oct. 31, 2002).

http://www.qiagen.com/clinical/applications/technologies/multiplex_pcr.asp "Molecular Diagnostics Research and Clinical Research." (Oct. 31, 2002).

Kebelmann-Betzing et al., "Advantages of a new *Taq* DNA Polymerase in Multiplex PCR and Time-Release PCR," *Biotechniques* vol. 24 No. 1: pp. 154-158 (1998).

Thelwell et al., "Mode of Action and Application of Scorpion Primers to Mutation Detection," *Nucleic Acids Research* vol. 28 No. 19: pp. 3752-3761 (2000).

Whitcombe et al., "Detection of PCR Products Using Self-Probing Amplicons and Fluorescense," *Nature Biotechnology* vol. 17: pp. 804-807 (Aug. 1999).

Zangenberg et al., "Improved Multiplex PCR of Plymorphic Markers," http://www.promega.com/geneticidproc/ussymp7proc/ab73.html (Oct. 31, 2002).

Baskaran et al., "Uniform Amplification of a Mixture of Deoxyribonucleic Acids with Varying GC Content," *Genome Research* vol. 6 No. 7: pp. 633-638 (Jul. 1996).

Brookes et al., "Cloning the Shared Components of Complex DNA Resources," *Human Molecular Genetics* vol. 3 No. 11: pp. 2011-2017 (1994).

Broude et al., "Multiplex Allele-Specific Target Amplification Based on PCR Suppression," *Proclamation of the National Academy of Sciences of the USA* vol. 98: pp. 206-211 (2001).

Chamberlain et al., "Deletion Screening of the Duchenne Muscular Dystrophy Locus via Multiplex DNA Amplification," *Nucleic Acids Research* vol. 16 No. 23: pp. 11141-11156 (1988).

Fan et al., "Parallel Genotyping of Human SNPs Using Generic High-Density Oligonucleotide Tag Arrays," *Genome Research* vol. 10: pp. 853-860 (2000).

Henegariu et al., "Multiplex PCR: Critical Parameters and Step-by-Step Protocol," *Biotechniques* vol. 23 No. 3: pp. 504-511 (1997).

Markoulatos et al., "Multiplex Polymerase Chain Reaction: A Practical Approach," *J. Clin. Lab. Anal.* vol. 16: pp. 47-51 (2002).

Shoemaker et al., "Quantitative Phenotypic Analysis of Yeast Deletion Mutants Using a Highly Parallel Molecular Bar-Coding Strategy," *Nature Genetics* vol. 14 No. 4: pp. 450-456 (1996).

Tatusova et al., "Blast 2 Sequences—A New Tool for Comparing Protein and Nucleotide Sequences," *FEMS Microbiology Letters* vol. 174: pp. 247-250 (1999).

Brownie, J. et al. "The elimination of primer -dimer accumulation in PCR" Nuc. Acids Res., Oxford University Press, vol. 25, No. 16, 3235-3241 (1997).

Peale, F. et al. "Multiplex display polymerase chain reaction amplifies and resolves related sequences sharing a single moderately conserved domain" Anal Biochem. vol. 256, No. 2, 158-168, (1998).

Broude, N.E., "Stem-loop oligonucleotides: a robust tool for molecular biology and biotechnology," Trends in Biotechnology, 20-6: 249-256, (2002).

\* cited by examiner

MULTIPLEX OLIGONUCLEOTIDE ADDITION AND TARGET AMPLIFICATION

CROSS-REFERENCE TO RELATED APPLICATIONS

This application claims the benefit of U.S. provisional application Ser. No. 60/331,693, filed Nov. 19, 2001, the disclosure of which is incorporated herein by reference in its entirety.

BACKGROUND OF THE INVENTION

Over the past two decades, the in vitro amplification of specific nucleic acids has become an essential tool for molecular biologists.

More recently, multiplexed amplification, in which a plurality of nucleic acid sequences are amplified in a single reaction, Chamberlain et al., *Nucl. Acid Research* 16(23): 11141–1156 (1988); U.S. Pat. No. 5,582,989, has become increasingly important. For example, multiplexed amplification, particularly multiplexed polymerase chain reaction (PCR), has been used to provide genetic fingerprints of infectious disease organisms. Other applications, such as multiplex SNP genotyping and variation scanning (for example, by mismatch repair detection), also greatly benefit from PCR multiplexing.

In its original implementation, multiplex PCR reactions include a specific primer pair for each locus to be amplified. These approaches have been plagued with problems, however, including uneven or failed amplification of some templates (especially those having GC rich-sequences), preferential amplification of other templates, poor sensitivity and specificity, poor reproducibility, and the generation of spurious amplification products (Henegariu et al., *BioTechniques* 23(3): 504–511 (1997); Markoulatos et al., *J. Clin. Lab. Anal.* 16: 47–51 (2002)).

Various modifications to the original approach have been developed in efforts to minimize these problems.

Among these modifications are changes to the reaction conditions, including adjustment of primer concentrations, $MgCl_2$ and dNTP concentrations, changes in PCR buffer concentrations, balance between $MgCl_2$ and dNTP concentrations, amounts of template DNA and Taq DNA polymerase, extension and annealing time and temperature, and the addition of adjuvants (Henegariu et al., *BioTechniques* 23(3): 504–511 (1997); Markoulatos et al., *J. Clin. Lab. Anal.* 16: 47–51 (2002)). Other strategies used include subcycling temperatures between high and low temperatures below the denaturation temperature, used during the annealing and elongation steps (U.S. Pat. No. 6,355,422), and the use of one sequence-specific primer and one common primer (Broude et al., *Proc. Natl. Acad. Sci. USA* 98, 206–211 (2001)).

The intractability of GC-rich sequences to multiplex PCR has also been addressed by a method in which addition of betaine and dimethylsulfoxide (DMSO) to the PCR reaction mix is said to allow more uniform amplification from a heterogeneous population of DNA molecules, many of which were GC-rich (Baskaran et al., *Genome Research* 6: 633–638 (1996)).

Yet other approaches alter the primers.

In one such effort, chimeric oligonucleotides are used as primers: the oligonucleotides include a 3' domain that is complementary to template, conferring template specificity, and a 5' domain that is noncomplementary to template; the 5' domain includes a sequence used to prime extension in rounds of PCR amplification subsequent to the first.

In this latter scheme, however, the cycles of amplification following the first amplify whatever product is generated in the first cycle, whether correct or erroneous. Thus, while the technique allows for more uniform amplification, it does not address the problem of spurious products.

In an analogous approach designed to clone the shared components in two complex samples, Brookes et al., *Human Molec. Genetics* 3(11):2011–2017 (1994), ligate primers to template ends generated by restriction fragment digestion.

None of the above-mentioned approaches, however, fully solves the problems associated with multiplex PCR.

Thus, there is a continuing need in the art for a method that allows the specific and uniform amplification of multiple nucleic acid sequences in a single reaction, without the generation of spurious products.

SUMMARY OF THE INVENTION

The present invention solves these and other problems in the art by providing, methods for appending one or more oligonucleotides directly to a single stranded nucleic acid template, typically (but not invariably) at one or more defined sites internal to the template. The oligonucleotides may be designed to provide one or more sites for priming the subsequent amplification of adjacent template regions. The methods may be readily multiplexed, permitting oligonucleotides to be appended, in a single reaction, to a plurality of templates. In multiplex embodiments in which the appended oligonucleotides provide one or more common priming sites, the plurality of templates may then be concurrently amplified using primers common to all templates. Such multiplexed amplification reactions provide high specificity and uniform amplification of all templates, solving problems that have plagued multiplex amplification reactions since the invention of PCR.

In a first aspect, the invention thus provides a method of appending at least a first oligonucleotide directly to a nucleic acid template.

The method comprises concurrently annealing the template and at least a first oligonucleotide to at least a first probe.

The probe includes at least a first template complementarity region and at least a first oligo positioning region directly adjacent thereto. The nucleotide of the template complementarity region and the nucleotide of the oligo positioning region that are directly adjacent within the probe define a first probe junction therebetween, and are termed first junctional nucleotides.

The oligonucleotide includes a terminal region that is complementary to the first oligo positioning region of the probe. The terminal nucleotide of the terminal oligonucleotide region is annealed in the hybridization reaction to the first junctional nucleotide of the probe's first oligo positioning region.

In a second step, a first ligatable free end is created at the template nucleotide that is annealed to the junctional nucleotide of the probe's first template complementarity region.

In the next step, the first oligonucleotide is ligated to the template's first free end.

In certain useful embodiments, the probe includes a second oligo positioning region directly adjacent to the first template complementarity region, the nucleotide of the template complementarity region and the nucleotide of the second oligo positioning region that are directly adjacent within the probe being second junctional nucleotides that define a second probe junction therebetween.

In these latter embodiments, a second oligonucleotide may usefully be appended to the template by annealing a second oligonucleotide to the first probe concurrently with annealing of the template to the probe. The second oligonucleotide includes a terminal region that is complementary to the second oligo positioning region of the probe, the terminal nucleotide of the terminal oligonucleotide region being annealed to the junctional nucleotide of the probe's second oligo positioning region.

In subsequent steps, a second ligatable free end is created at the template nucleotide that is annealed to the second junctional nucleotide of the probe's first template complementarity region; and then the second oligonucleotide is ligated to the template's second free end.

The ligatable free ends may be created by removing template regions that are noncomplementary to the probe's first complementarity region, as by exonucleolytic digestion, such as digestion with Exonuclease VII or a combination of Exonuclease T and rec $J_f$. Alternatively, in some embodiments the template regions that are noncomplementary to probe may be removed by digestion with a single-strand specific endonuclease, such as mung bean nuclease.

Usefully, the methods of this aspect of the invention may further comprise the step, after ligating, of separating the template from the probe and oligonucleotides.

In some embodiments, the probe further comprises means for separating the probe from the template.

Such separation means include incorporation of a plurality of deoxyuridine residues. In these embodiments, the separating step comprises cleaving the probe at its deoxyuridine residues into a plurality of probe fragments, and then size separating the template from the probe fragments and from the oligonucleotides.

In other embodiments, the separating means may be one or more capture moieties, such as biotin.

The methods may further include the step, after separating template from probe and oligonucleotides, of amplifying a region of the template between the first and second appended oligonucleotides.

In such embodiments, the first oligonucleotide typically has a first priming site and the second oligonucleotide has a second priming site, and the amplification step is performed by priming polymerization at both the first and second priming sites. Typically, such amplification is performed using PCR.

The template may be derived from cDNA or genomic DNA, from a single individual or from a plurality of individuals. The template may, for example, be genomic DNA derived from a eukaryote, such as a human being.

To facilitate specific detection of amplified products, at least one of the first and second oligonucleotides may include a bar code sequence.

The methods of the invention may readily be multiplexed.

Thus, in a second aspect, the invention provides a method of appending at least a first oligonucleotide directly to each of a plurality of nucleic acid templates of distinct sequence in a single reaction.

The method comprises concurrently annealing each template and a respective first oligonucleotide to a respective one of a plurality of probes within a single reaction mixture.

Each probe includes at least a first region of complementarity to a respective one of the templates and at least a first oligo positioning region directly adjacent thereto. The nucleotide of the template complementarity region and the nucleotide of the oligo positioning region that are directly adjacent within the probe are termed first junctional nucleotides and define a first probe junction therebetween.

Each of the first oligonucleotides includes a terminal region that is complementary to the first oligo positioning region of a respective probe, the terminal nucleotide of the oligonucleotide region being annealed to the first junctional nucleotide of the probe's first oligo positioning region.

Following hybridization, a first ligatable free end is created in each template at the nucleotide that is annealed to the junctional nucleotide of the template's respective probe's first template complementarity region.

Thereafter, each of the first oligonucleotides is ligated to its respective template's first free end.

As in the uniplex (singleplex) aspects of the present invention, in additional multiplex embodiments each probe may include a second oligo positioning region directly adjacent to the first template complementarity region, the nucleotide of the template complementarity region and the nucleotide of the second oligo positioning region that are directly adjacent within the probe being second junctional nucleotides that define a second probe junction therebetween.

In these latter embodiments, a second oligonucleotide is appended to each of the plurality of templates of distinct sequence by annealing a respective second oligonucleotide to each probe concurrently with annealing of the template to the probe. The second oligonucleotide includes a terminal region that is complementary to the second oligo positioning region of its respective probe, the terminal nucleotide of the terminal oligonucleotide region being annealed to the junctional nucleotide of the probe's second oligo positioning region.

Thereafter, a second ligatable free end is created in each of the templates at the nucleotide that is annealed to the second junctional nucleotide of the respective probe's first template complementarity region. Then the second oligonucleotide is ligated to the template's second free end.

Usefully, each of the first and/or second oligonucleotides includes a priming sequence that is common thereamong.

The ligatable free ends may be created, in certain embodiments, by removing template regions that are noncomplementary to the probe's first complementarity region. In some embodiments, template noncomplementary regions are removed by exonucleolytic digestion; in others, by endonucleolytic digestion.

The multiplex embodiments may include a further step of separating templates from their respective probes and oligonucleotides, and may further include a later step of concurrently amplifying a region of each said template.

Amplification may, in certain embodiments, be performed by priming polymerization at the first common priming site and the second common priming site. In such embodiments, amplification is typically by polymerase chain reaction (PCR).

The multiplex methods of the present invention may include at least 10 templates of distinct sequence, at least 100 templates of distinct sequence, at least 1000 templates of distinct sequence, or more. Usefully, at least one of the first and second oligonucleotides comprises a bar code sequence, thus allowing concurrent detection of all amplified templates.

In other embodiments, a bar code is appended to the template separately from the oligonucleotide that appends a priming sequence to the template.

In these embodiments, either or both of the probe's oligo positioning regions may include a first and a second subregion. One of the subregions is complementary in sequence to the oligonucleotide to be appended; the other of the subregions is complementary in sequence to a further oligonucleotide that includes the bar code tag.

A ligatable free end is created in the template, and the bar code oligonucleotide ligated thereto. In the same or subsequent step, the priming oligonucleotide is ligated to the bar code oligonucleotide.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which.

DETAILED DESCRIPTION OF THE INVENTION

The present invention provides methods for appending one or more oligonucleotides directly to a single stranded nucleic acid template, typically (but not invariably) at one or more defined sites internal to the template. The oligonucleotides may be designed to provide one or more sites for priming the subsequent amplification of adjacent template regions. The methods may be readily multiplexed, permitting oligonucleotides to be appended, in a single reaction, to a plurality of templates. In multiplex embodiments in which the appended oligonucleotides provide one or more common priming sites, the plurality of templates may then be concurrently amplified using primers common to all templates. Such multiplexed amplification reactions provide high specificity and uniform amplification of all templates, solving problems that have plagued multiplex amplification reactions since the invention of PCR.

In a first aspect, the invention provides a method of appending at least a first oligonucleotide directly to a nucleic acid template.

The method may conveniently be understood by reference to the illustrative reaction of FIG. 1, in which oligonucleotide 20 is appended to a distinct site internal to template 10.

Figure 1A:
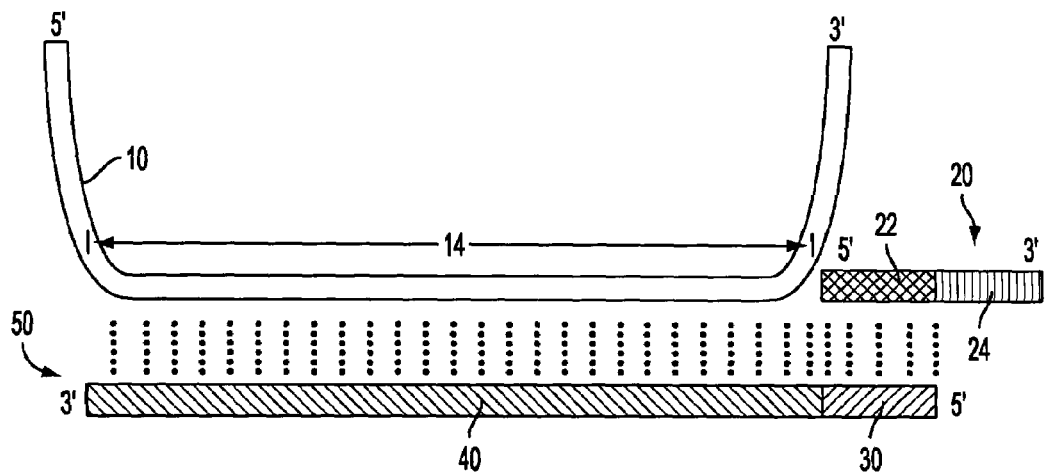
FIG. 1 is a schematic representation illustrating a method for appending a first oligonucleotide directly to a single-stranded nucleic acid template, according to the present invention. In this and all schematic representations herein, dotted vertical lines extending between hybridized nucleic acid strands are intended to indicate base pairing generally; the number of lines is not intended to reflect any specific number of basepairs.

In the first step of the method, illustrated in FIG. 1A, template 10 and at least first oligonucleotide 20 are concurrently annealed to first probe 50.

Probe 50 includes at least first template complementarity region 40 and at least first oligo positioning region 30 directly adjacent thereto: in the annealing step, template region 14 hybridizes to template complementarity region 40 of probe 50 and oligonucleotide region 22 concurrently hybridizes to oligo positioning region 30 of probe 50.

Figure 2A:
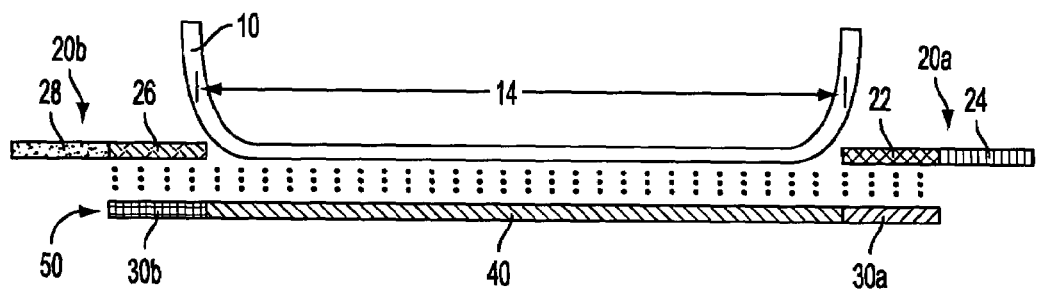
FIG. 2 is a schematic representation illustrating a method for appending a first and a second oligonucleotide directly to a single-stranded nucleic acid template, according to the present invention.
Figure 2B:
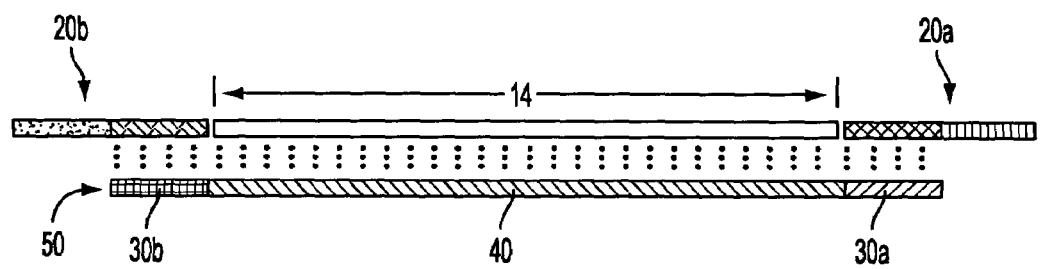
Figure 2C:

The nucleotide of template complementarity region 40 and the nucleotide of oligo positioning region 30 that are directly adjacent within probe 50 define a junction within probe 50, and are hereinafter termed junctional nucleotides. In embodiments of the methods of the present invention in which two oligonucleotides are appended to template 10, as is illustrated in FIG. 2, first oligo positioning region 30a directly abuts template complementarity region 40 at a first probe junction, and second oligo positioning region 30b directly abuts template complementarity region 40 at a second probe junction. In such embodiments, the abutting nucleotides are thus respectively denominated first junctional nucleotides and second junctional nucleotides.

Oligonucleotide 20 (synonymously, "oligo 20") includes terminal region 22 that is complementary in sequence to oligo positioning region 30 of probe 50. Oligo 20 may optionally include a further region 24. The terminal nucleotide of oligonucleotide region 22—in the orientation schematized in FIG. 1, the 5' terminal nucleotide of oligo 20—is annealed to the junctional nucleotide of probe 50's first oligo positioning region 30.

Oligo 20 is typically further designed to include at least one sequence to which an oligonucleotide primer can later anneal (a "priming site").

In the next step of the method, a first ligatable free end is created in template 10 at the nucleotide of template region 14 that is annealed to the junctional nucleotide of template complementarity region 40 of probe 50. The template nucleotide at which the free end is created remains within template 10.

Figure 1B:
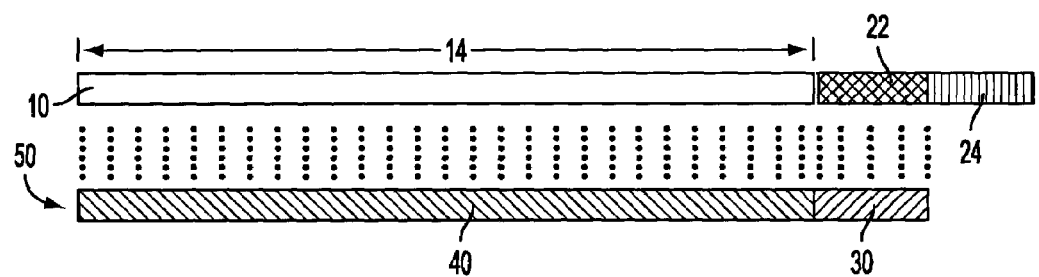

The products resulting from this step are shown in FIG. 1B, illustrating that the newly created ligatable free end of template 10 and the terminal nucleotide of oligonucleotide 20 terminal region 22 are positioned directly adjacent to one another by concurrent hybridization to probe 50 regions 40 and 30, respectively.

Figure 1C:

In a final step, first oligonucleotide 20 is ligated to the first ligatable free end of template 10, with results as schematized in FIG. 1C.

In the methods of the present invention, template 10 is a single-stranded nucleic acid, typically DNA, and may be obtained by denaturation of double-stranded nucleic acids.

Template 10 may, for example, be derived from cDNA. Template 10 may be derived directly from single-stranded cDNA, such as that obtained by first strand synthesis from mRNA transcripts, or from cDNA rendered single-stranded by denaturation of double-stranded cDNA obtained either directly after second strand cDNA synthesis or from prior-cloned double stranded cDNA.

Template 10 may in other embodiments be derived from genomic DNA, either from a genomic DNA preparation prepared directly from cells or from genomic DNA that has been prior-cloned. Typically, genomic DNA is first denatured, e.g. by heat or treatment with base, to provide single stranded template 10.

Template 10 may be derived from a single individual or pooled from a plurality of individuals. Templates from a single individual are useful, for example, in genotyping or haplotyping efforts, as may be practiced in molecular genetic diagnosis or prognosis. Pooled templates are useful in SNP discovery efforts, and may usefully be pooled from at least 10 individuals, 100 individuals, even 1000 individuals or more.

Template 10 may usefully be derived from nucleic acids drawn from a prokaryote, eukaryote, or virus.

Prokaryotes include both archaebacteria and eubacteria, including both gram negative and gram positive eubacteria, and the methods of the present invention find particular utility when template 10 is drawn from nucleic acids of pathogenic prokaryotes.

Among eukaryotes, template 10 may usefully be drawn from protozoa, fungi, insects, plants, and animals, including fungi selected from the group consisting of *Saccharomyces cerevisiae, Schizosaccharomyces pombe, Ustillago maydis, Neurospora crassa* and *Candida albicans;* insects selected from the group consisting of *Drosophila melanogaster* and *Anopheles* species; plants selected from the group consisting of experimental model plants such as *Chlamydomonas reinhardtii, Physcomitrella patens,* and *Arabidopsis thaliana,* crop plants such as cauliflower (*Brassica oleracea*), artichoke (*Cynara scolymus*), fruits such as apples (*Malus,* e.g. *domesticus*), mangoes (*Mangifera,* e.g. *indica*), banana (*Musa,* e.g. *acuminata*), berries (such as currant, *Ribes,* e.g. *rubrum*), kiwifruit (*Actinidia,* e.g. *chinensis*), grapes (*Vitis,* e.g. *vinifera*), bell peppers (*Capsicum,* e.g. *annuum*), cherries (such as the sweet cherry, *Prunus,* e.g. *avium*), cucumber (*Cucumis,* e.g. *sativus*), melons (*Cucumis,* e.g. *melo*), nuts (such as walnut, *Juglans,* e.g. *regia;* peanut, *Arachis hypogeae*), orange (*Citrus,* e.g. *maxima*), peach (*Prunus,* e.g. *persica*), pear (*Pyra,* e.g. *communis*), plum (*Prunus,* e.g. *domestica*), strawberry (*Fragaria,* e.g. *moschata* or *vesca*), tomato (*Lycopersicon,* e.g. *esculentum*); leaves and forage, such as alfalfa (*Medicago,* e.g. *sativa* or *truncatula*), cabbage (e.g. *Brassica oleracea*), endive (*Cichoreum,* e.g. *endivia*), leek (*Allium,* e.g. *porrum*), lettuce (*Lactuca,* e.g. *sativa*), spinach (*Spinacia,* e.g. *oleraceae*), tobacco (*Nicotiana,* e.g. *tabacum*); roots, such a's arrowroot (*Maranta,* e.g. *arundinacea*), beet (*Beta,* e.g. *vulgaris*), carrot (*Daucus,* e.g. *carota*), cassava (*Manihot,* e.g. *esculenta*), turnip (*Brassica,* e.g. *rapa*), radish (*Raphanus,* e.g. *sativus*), yam (*Dioscorea,* e.g. *esculenta*), sweet potato (*Ipomoea batatas*); seeds, including oilseeds, such as beans (*Phaseolus,* e.g. *vulgaris*), pea (*Pisum,* e.g. *sativum*), soybean (*Glycine,* e.g. *max*), cowpea (*Vigna unguiculata*), mothbean (*Vigna aconitifolia*), wheat (*Triticum,* e.g. *aestivum*), sorghum (*Sorghum* e.g. *bicolor*), barley (*Hordeum,* e.g. *vulgare*), corn (*Zea,* e.g. *mays*), rice (*Oryza,* e.g. *sativa*), rapeseed (*Brassica napus*), millet (*Panicum* sp.), sunflower (*Helianthus annuus*), oats (*Avena sativa*), chickpea (*Cicer,* e.g. *arietinum*); tubers, such as kohlrabi (*Brassica,* e.g. *oleraceae*), potato (*Solanum,* e.g. *tuberosum*) and the like; fiber and wood plants, such as flax (*Linum* e.g. *usitatissimum*), cotton (*Gossypium* e.g. *hirsutum*), pine (*Pinus* sp.), oak (*Quercus* sp.), eucalyptus (*Eucalyptus* sp.), and the like and ornamental plants such as turfgrass (*Lolium,* e.g. *rigidum*), petunia (*Petunia,* e.g. x *hybrida*), hyacinth (*Hyacinthus orientalis*), carnation (*Dianthus* e.g. *caryophyllus*), delphinium (*Delphinium,* e.g. *ajacis*), Job's tears (*Coix lacryma-jobi*), snapdragon (*Antirrhinum majus*), poppy (*Papaver,* e.g. *nudicaule*), lilac (*Syringa,* e.g. *vulgaris*), hydrangea (*Hydrangea* e.g. *macrophylla*), roses (including Gallicas, Albas, Damasks, Damask Perpetuals, Centifolias, Chinas, Teas and Hybrid Teas) and ornamental goldenrods (e.g. *Solidago* spp.); and animals selected from the group consisting of mammals, such as primates, including humans, monkeys, and apes, small laboratory animals, including rodents, such as mouse or rat, guinea pigs, lagomorphs, such as rabbits, livestock, such as cows, horses, chickens, geese, turkeys, goats, and sheep, and domestic pets, such as dogs and cats.

Template 10 may also usefully be derived from viral nucleic acids, including viruses selected from the group consisting of double-stranded DNA viruses, such as herpesviruses, including human herpesvirus 1 and 2 (HSV-1 and HSV-2), varicella-zoster (HSV-3), cytomegalovirus (HCMV), human herpesvirus 6, 7, 8 (HHV-6, HHV-7, HHV-8), and Epstein-Barr virus (EBV), retroviruses, including mammalian type B retroviruses, such as mouse mammary tumor virus; mammalian type C retroviruses, such as murine leukemia virus and reticuloendotheliosis virus (strain T, A); avian type C retroviruses such as avian leukosis virus; type D retroviruses such as Mason-Pfizer monkey virus; BLV-HTLV retroviruses such as bovine leukemia virus; lentiviruses, such as bovine lentiviruses including bovine immunodeficiency virus, feline immunodeficiency virus, visna/maedi virus (strain 1514), and primate lentiviruses such as human immunodeficiency virus 1 (HIV1), human immunodeficiency virus 2 (HIV2), and simian immunodeficiency virus (SIV), and other types of pathogenic viruses.

Template 10 is typically at least about 40 nt in length, often at least 50, 75, 100, 125 or 150 nt in length, at times at least about 200 nt, 300 nt, 400 nt, or 500 nt or more in length, and when derived from genomic nucleic acid can be at least 1000 nt (1 kb), 2 kb, 3 kb, 4 kb, 5 kb, 10 kb, 20 kb, 30 kb, 40 kb or 50 kb in length.

Probe 50 includes at least first template complementarity region 40.

Template complementarity region 40 of probe 50 is designed to have sufficient length and sufficient sequence complementarity to a region of template 10 as to permit annealing of probe 50 to template 10 under hybridization conditions of desired stringency. The region of template 10 to which probe template complementary region 40 hybridizes is defined as template region 14.

Template complementarity region 40 of probe 50 is typically at least 20 nt in length, more typically at least 35, 40, 45, or 50 nt in length, often at least 100 nt in length, 150 nt in length, even at least 200 nt, 300 nt, 400 nt, or even at least 500 nt or more in length. Template complementarity region 40 of probe 50 is typically no more than about 1000 nt in length, typically no more than about 500 nt in length, often no more than 400 nt, 300 nt, 200 nt, even no more than 100 nt in length.

The length of template complementarity region 40 of probe 50 may further be chosen so as to hybridize to a region 14 of template 10 that includes the entirety of a template portion de4sired to be amplified.

Template complementarity region 40 of probe 50 is further designed to have sufficient sequence complementarity to template region 14 as to permit annealing of probe 50 to template 10 under hybridization conditions of desired stringency.

Template complementarity region 40 of probe 50 may, for example, be perfectly (that is, 100%) complementary in sequence to template region 14. Template complementarity region 40 may, in the alternative, be only at least 95% complementary, 90% complementary, 85% complementary, 80% complementary, even only at least 75% complementary in sequence to template region 14, with percent complementarity measured for the purposes of the present invention by the procedure of Tatiana et al., *FEMS Mirobiol. Lett.* 174: 247–250 (1999), which procedure is effectuated by the computer program BLAST 2 SEQUENCES, available online at the National Center for Biotechnology Information (NCBI) website.

With a pooled template, template complementarity region 40 of probe 50 may simultaneously have different degrees of sequence complementarity to various of the template regions 14 in the pooled template sample.

Probe 50 further includes at least first oligo positioning region 30.

First oligo positioning region 30 of probe 50 is typically at least about 10 nt, 11 nt, 12 nt, 13 nt, 14 nt, 15 nt, even 16, 17, 18, 19, or 20 nt in length, and may be at least 25 nt, 30 nt, 40 nt, or even at least 50 nt in length or more. First oligo positioning region 30 of probe 50 is typically no more than about 50 nt in length, even more typically no more than about 40 nt in length, and may be no more than 35, 30, or even 25 nt in length.

In the illustration of FIG. 1, first oligo positioning region 30 is positioned 5' to template complementarity region 40. This orientation is not required: first oligo positioning region 30 may be positioned 3' to template complementarity region 40.

Probe 50 may be synthesized chemically, using solid phase procedures well known in the art, or by ligation of smaller, chemically-synthesized fragments.

Typically, however, probe 50 is generated by first cloning the template complementarity region into a replicable vector, and then using flanking vector primers to amplify the sequence in a PCR reaction. To permit separation of template from probe after oligonucleotide ligation, the PCR reaction may usefully be performed using dUTP instead of dTTP; removal of uracil-containing probes from template is further described below.

Oligonucleotide 20 is typically at least 15, 20, or 25 nt in length, and may be at least 30 nt, 35 nt, 40 nt, even at least 50 nt in length. Oligonucleotide 20 is typically no more than 50 nt in length, and often no more than 40, 30, even no more than 25 nt in length.

Terminal region 22 of oligo 20 is designed to have sufficient length and sufficient sequence complementarity to probe region 30 as to permit annealing of oligo 20 to probe 50 under hybridization conditions of desired stringency.

Terminal region 22 of oligo 20 is typically at least about 10 nt, 11 nt, 12 nt, 13 nt, 14 nt, 15 nt, even 16, 17, 18, 19, or 20 nt in length, and may be at least 25 nt, 30 nt, 40 nt, or even at least 50 nt in length or more, and is typically no more than about 50 nt in length, even more typically no more than about 40 nt in length, and may be no more than 35, 30, or even 25 nt in length.

Terminal region 22 of oligo 20 is further designed to have sufficient sequence complementarity to probe region 30 as to permit annealing of oligo 20 to probe 50 under hybridization conditions of desired stringency.

Oligonucleotide terminal region 22 may, for example, be perfectly (that is, 100%) complementary in sequence to probe region 30. oligo region 22 may, in the alternative, be only at least 95% complementary, 90% complementary, 85% complementary, 80% complementary, even only at least 75% complementary in sequence to probe region 30.

Oligonucleotide 20 may optionally include a further region 24 that is noncomplementary in sequence to probe 50. This additional region 24 of oligonucleotide 20 may, for example, usefully include one or more restriction sites to facilitate subsequent cloning of portions of template 10 and may, in addition or in the alternative, include promoter sequences for phage RNA polymerases, such as T3, T7, and SP6 polymerases.

Oligo 20 is typically further designed to include a sequence, a "priming site", to which an oligonucleotide primer can anneal in later steps.

The priming site may be coextensive with either or both of terminal region 22 and optional region 24, or may be only a portion thereof. The length and sequence of the priming site sequence are chosen based upon considerations well known in the art, including the calculated Tm of the duplex expected between priming site and primer, the absence of the priming site sequence or its reverse complement in templates desired to be amplified, and the like.

Annealing conditions for the first step of the methods of the present invention are chosen so as to permit concurrent annealing of template 10 and oligonucleotide 20 to probe 50. Typically, but not invariably, oligonucleotide terminal region 22 will be shorter than template region 14, and annealing conditions will thus be chosen principally to ensure that oligonucleotide 20 hybridizes to probe 50 with desired stringency.

In the next step of the method, a first ligatable free end is created in template 10 at the nucleotide of template region 14 that is annealed to the junctional nucleotide of template complementarity region 40 of probe 50.

In one series of embodiments, the ligatable free end is created by removing template regions that are noncomplementary to probe region 40, typically by treatment with nucleases active on single-stranded substrates.

Usefully, ligatable free ends are created using exonucleolytic digestion, with the choice of nuclease determined by the desired direction (or directions) of template exonucleolytic digestion. For example, regions of template noncomplementarity to probe 50 may be removed by reaction with Exo I (3' to 5' exonuclease), Exo T (3' to 5'), rec $J_f$ (5' to 3'), Exo VII (both 3' to 5' and 5' to 3' exonuclease activity), and combinations thereof.

In embodiments in which the only regions of template noncomplementarity to probe 50 are external to template region 14 (as in FIGS. 1 and 2, in contrast to FIG. 4, further described below), the ligatable free ends may also readily be created by use of an endonuclease, such as mung bean nuclease.

In embodiments in which the free end is formed at the 5' end of template region 14, a further step of kinasing the template free end may be performed to ensure the presence of a 5' phosphate for subsequent ligation.

First oligonucleotide 20 is then ligated to the newly created first ligatable free end of template 10 using a DNA ligase such as T4 ligase or, usefully, a thermostable ligase such as Taq ligase. Selection of ligase and ligation conditions are well within the skill in the art.

The method for appending an oligonucleotide directly to a template, as schematized in FIG. 1 and described above, may be repeated, effecting the addition of a second oligonucleotide to the template.

FIG. 2 shows an alternative series of embodiments in which first and second oligonucleotides 20a and 20b, respectively, are appended to template 10 in a single reaction.

In these latter embodiments, probe 50 further includes second oligo positioning region 30b, additional to first oligo positioning region 30a. Second oligo positioning region 30b is directly adjacent to first template complementarity region 40. The nucleotide of template complementarity region 40 and the nucleotide of second oligo positioning region 30b that are directly adjacent within probe 50 define a second junction within probe 50, and are hereinafter termed second junctional nucleotides.

Second oligo 20b includes terminal region 26 that is complementary in sequence to second oligo positioning region 30b of probe 50.

Second oligo 20b may, like first oligo 20a, optionally include a further region 28 that is noncomplementary in sequence to probe 50. This additional region 28 of oligonucleotide 20 may, for example, usefully include one or more restriction sites to facilitate subsequent cloning of portions of template 10 and may, in addition or in the alternative, include promoter sequences for phage RNA polymerases, such as T3, T7, and SP6 polymerases.

Second oligo 20b is typically further designed to include at least one site for subsequent priming of enzymatic polymerization.

The priming site may be coextensive with either or both of terminal region 26 and optional region 28, or may be only a portion thereof. The length and sequence of the priming site sequence are chosen based upon considerations well known in the art, including the calculated Tm of the duplex expected between priming site and primer, the absence of the priming site sequence or its reverse complement in templates desired to be amplified, and the like.

Template 10, first oligo 20a, and second oligo 20b are concurrently annealed to first probe 50.

Template 10 anneals to probe 50 through hybridization of template region 14 to probe region 40, the template complementarity region. Terminal region 22 of first oligonucleotide 20a anneals to first oligo positioning region 30a, as in the embodiments above-described, and terminal region 26 of second oligo 20b anneals to second oligo positioning region 30b. The terminal nucleotide of first oligonucleotide terminal region 22 is annealed to the junctional nucleotide of the probe's first oligo positioning region. The terminal nucleotide of the second oligonucleotide's terminal region 26 is annealed to the junctional nucleotide of the probe's second oligo positioning region.

In the next step, first and second ligatable free ends are created on template 10. The first ligatable free end is created in template 10 at the nucleotide of template region 14 that is annealed to the first junctional nucleotide of template complementarity region 40 of probe 50. The second ligatable free end is created in template 10 at the nucleotide of template region 14 that is annealed to the second junctional nucleotide of template complementarity region 40 of probe 50. The template nucleotides at which the free ends are created remain within the template.

Thereafter, both first and second oligonucleotides are ligated to template 10: the first oligonucleotide to the first ligatable free end of template 10, the second oligonucleotide to the second ligatable free end of template 10.

Usefully, ligatable free ends are created using bidirectional exonucleolytic digestion, either from a single bidirectional exonuclease or a combination of exonucleases having opposite directions of exonuclease activity. In embodiments in which the only regions of template noncomplementarity to probe 50 are external to template region 14 (as in FIGS. 1 and 2, in contrast to FIG. 4, further described below), the ligatable free ends may also readily be created by use of an endonuclease, such as mung bean nuclease.

Figure 3A:
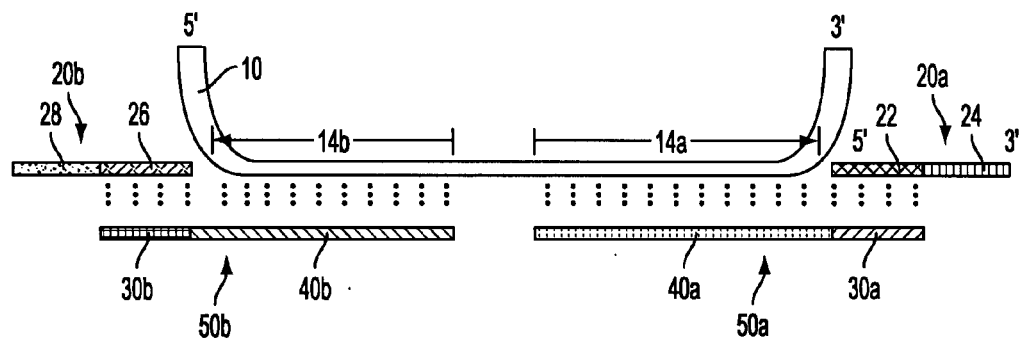
FIG. 3 is a schematic representation illustrating additional embodiments of methods for appending a first and a second oligonucleotide directly to a single-stranded nucleic acid template, according to the present invention.
Figure 3B:
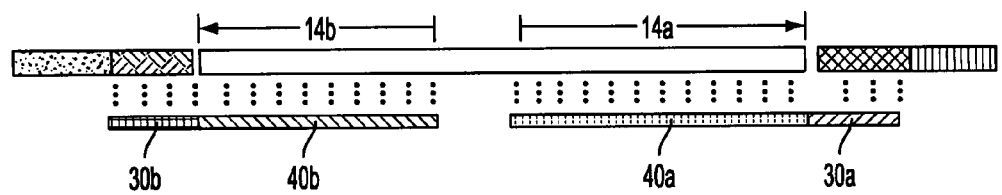

In another series of embodiments, illustrated in FIG. 3, first and second oligonucleotides are appended to template 10 in a single reaction using two probes, first probe 50a and second probe 50b.

First probe 50a includes template complementarity region 40a and first oligo positioning region 30a. Second probe 50b includes template complementarity region 40b and second oligo positioning region 30b. Template 10 hybridizes to probes 50a and 50b through template regions 14a and 14b, respectively.

Figure 3C:
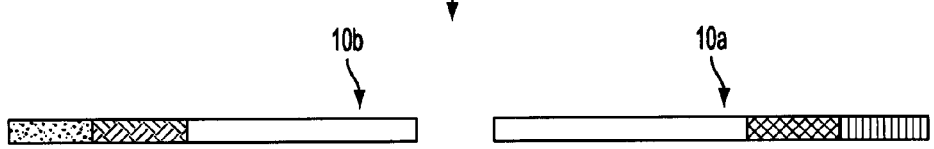

The subset of these embodiments in which template regions 14a and 14b are not contiguous within template 10, as is illustrated in FIG. 3, usefully permit oligonucleotides to be appended to template 10 independently of the sequence intervening between template regions 14a and 14b, and thus permit oligonucleotides to be appended to template 10 despite variations that occur within the intervening region, such as exon insertions or deletions. This is represented in FIG. 3C by the plurality of hybridized template regions 10a and 10b.

In such embodiments, exonuclease digestion, rather than endonuclease digestion, is typically used to create the first and second template ligatable free ends.

Figure 4A:
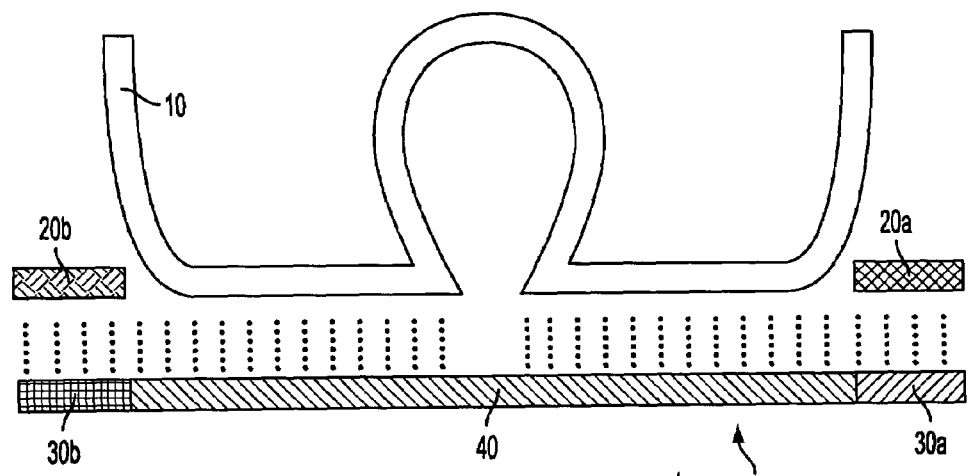
FIG. 4 is a schematic representation illustrating embodiments of methods for appending a first and a second oligonucleotide directly to a single-stranded nucleic acid template in which the template has discontinuous regions of complementarity to probe, according to the present invention.

FIG. 4 illustrates a further series of embodiments in which a single probe 50 is used to append first and second oligonucleotides to template 10. In contrast to the embodiments illustrated in FIG. 2, a region of noncomplementarity to probe interrupts template region 14.

Figure 4B:
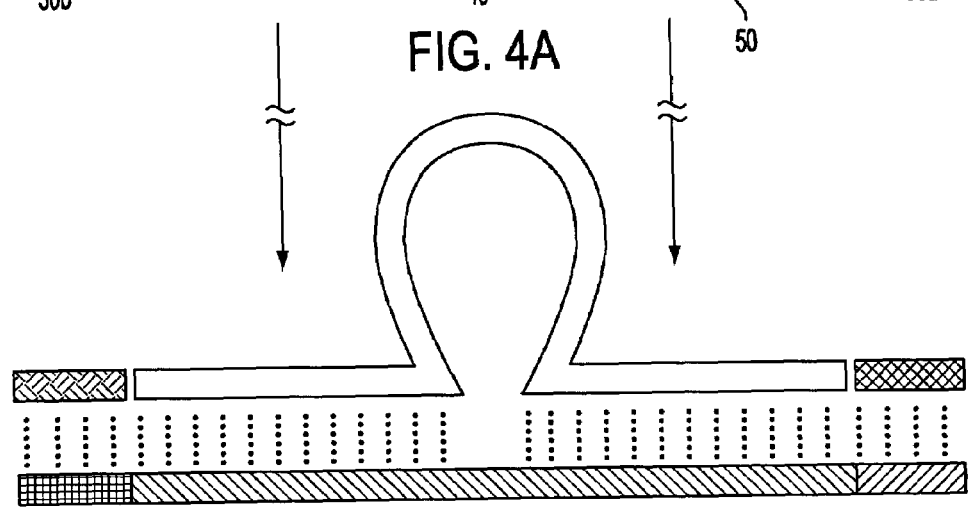

In such embodiments, exonuclease digestion may be used to create ligatable free ends in template 10, with results as schematized in FIG. 4B. Such embodiments usefully permit oligonucleotides to be appended to template 10 independently of the sequence interrupting template region 14, and thus permit oligonucleotides to be appended to template 10 despite variations such as exon insertions or deletions in this region.

Figure 4C:
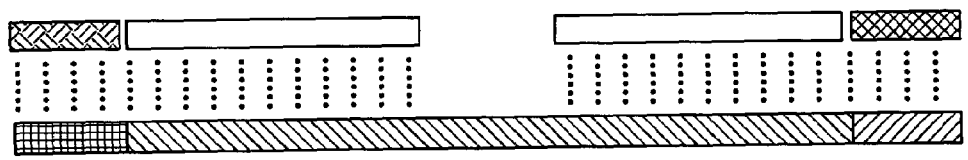

In alternative embodiments, endonuclease digestion, such as by mung bean nuclease, may be used to create first and second ligatable free ends, with results as schematized in FIG. 4C. In these embodiments, the endonuclease additionally removes the region of noncomplementarity that intervenes within template 10.

These latter embodiments, in which endonclease digestion is used to create ligatable free ends, permit templates that are perfectly matched to probe region 40 to be discriminated from templates that are imperfectly matched to probe region 40. In particular, when the method is followed by a step of bidirectional amplification, such as by PCR, only those templates that are perfectly matched to probe region 40 will be exponentially amplified; templates that are imperfectly matched will have been cleaved (as in FIG. 4C) and can at most be amplified unidirectionally, and thus geometrically.

In a further series of embodiments, a priming site may be appended to template 10 without ligation of an oligonucleotide 20. In these embodiments, which require that a free ligatable 3' end be present or created in template 10, the priming site is appended to template 10 by DNA polymerase extension directly from template 10, rather than by ligation of a separate oligonucleotide species. In this reaction, the oligo positioning region, referred to as 30 in previous figures, a plurality of which is referred to here as 30a and 30b of probe 50 acts as the "template" for directing enzymatic extension of template 10.

In such embodiments, the first hybridization step is performed without addition of first or second oligonucleotides. After hybridization of template 50 to probe, referred to as 30 in previous figures, a plurality of which is referred to here as 30a and 30b, a DNA polymerase, such as Taq polymerase, is added to extend the template to append a priming site and, optionally, a molecular barcode (bar codes are further described herein below). Typically, this polymerization step is followed by a second hybridization step with the addition of an oligonucleotide 20, followed by ligation, as in the embodiments above-described.

Any of the above-described embodiments may include a further step of separating template 10 from oligonucleotides 20 and probes 50.

Typically, template 10 is readily separated from oligonucleotides 20 based upon size, using standard techniques such as gel electrophoresis, gel filtration, dialysis, or centrifugation in spin columns having size-selective membranes.

In some embodiments, template 10 may also be separated from probes 50 based solely upon size differences. More typically, however, probe 50 includes means for separating the probe from template.

For example, probe 50 may include deoxyuridine residues as substitutes for all or for a fraction of thymidine residues.

In such embodiments, probe 50 may be treated after the ligation step with uracil-DNA glycosylase ("UDG"), which catalyzes the release of free uracil from uracil-containing DNA, creating apurinic ("AP") sites.

AP sites may then be cleaved enzymatically using an AP endonuclease or, under certain conditions, an AP lyase.

For example, the AP site may be cleaved using Endo IV or Fpg (formamidopyrimidine [fapy]-DNA glycosylase; also known as 8-oxoguanine DNA glycosylase). Fpg cleaves both 3' and 5' to the AP site, removing the AP site and leaving a 1 base gap.

Alternatively, the AP sites may be cleaved chemically, such as by treatment with 1,4 diaminobutane and heat.

In yet a further alternative, the probe can include purines such as 8-oxoguanine, 8-oxoadenine, fapy-guanine, methyl-fapy-guanine, fapy-adenine, aflatoxin B-fapy-guanine, 5-hydroxy-cytosine, and 5-hydroxy-uracil, that mimic damaged purines. Fpg glycosylase will release these residues from DNA and remove the resulting AP site, leaving a 1 nucleotide gap.

The cleavage products of probe 50 may then readily be separated from template 10 by size separation, optionally with a preceding denaturation step.

Probe 50 may instead, or in addition, include at least one capture moiety. The capture moiety is typically one member of a specific binding pair.

"Specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least two-fold, more typically by at least 10-fold, often at least 100-fold. Typically, the affinity or avidity of a specific binding reaction is least about $10^7$ $M^{-1}$, using at least $10^8$ $M^{-1}$ to at least about $10^9$ $M^{-1}$, and often greater, including affinities or avidities up to $10^{10}$ $M^{-1}$ to $10^{12}$ $M^{-1}$.

The phrase "specific binding pair" refers to pairs of molecules, typically pairs of biomolecules, that exhibit specific binding.

A wide range of specific binding pair members that can be used for capture of oligonucleotides are known in the art.

Among these are small capture moieties colloquially termed "haptens" irrespective of their antigenicity. Such haptens include biotin, digoxigenin, and dinitrophenyl. Biotin can be captured using avidin, streptavidin, captavidin, neutravidin, or anti-biotin antibodies. Digoxigenin and dinitrophenyl can be captured using antibodies specific for the respective hapten.

Capture of probe to a solid support, after ligation, permits separation of probe 50 from template 10 and oligonucleotides 20.

In another series of embodiments, oligonucleotides 20 may include one or more capture moieties. In such embodiments, template 10 is typically first separated from unligated oligos by size separation, and template 10 then separated from probe 50 by capture of template molecules to which oligonucleotides have been successfully ligated.

The methods of the present invention may include a further step, after ligating oligonucleotides to the template, of amplifying the template. Typically, the ligated template is first separated from probe and free oligonucleotides, and then amplified.

As used herein, the term amplification includes the production of RNA transcripts by polymerization driven from a phage promoter.

More typically, however, the amplification product is DNA produced by polymerization primed using one or more oligonucleotides ("primers") that are capable of hybridizing to one or more priming sites within one or more of the oligonucleotides appended to the template.

For example, a first primer capable of binding to a first priming site present in the first oligonucleotide may be used to prime unidirectional amplification. A second primer capable of binding to the complement of the second priming site present in the second oligonucleotide may be used concurrently to prime bidirectional amplification. In embodiments in which first and second priming sites are reverse complements of one another, the first and second primers may be the same.

Amplification may be isothermal or thermal cycling.

Nucleic acid amplification methods useful in the methods of the present invention are well known in the art and include, e.g., polymerase chain reaction (PCR), nucleic acid sequence-based amplification (NASBA), self-sustained sequence recognition (3SR), ligase chain reaction (LCR), transcription-mediated amplification (TMA), rolling circle amplification (RCA), and strand displacement amplification (SDA).

Typically, bidirectional amplification is effected using PCR.

The methods of the present invention may be readily multiplexed, permitting one or more oligonucleotides to be appended to a plurality of templates of distinct sequence in a single reaction. The templates may be separate nucleic acid molecules or separate loci of a single molecule such as a chromosome. In particularly useful multiplex embodiments, at least one, and typically two, common priming sites are appended to each of the plurality of templates.

Thus, in another aspect, the present invention provides methods for appending at least a first oligonucleotide directly to a plurality of nucleic acid templates of distinct sequence in a single reaction.

In such multiplex embodiments of the present invention, at least one oligonucleotide is appended to at least 2 templates of distinct sequence, typically at least 5 templates of distinct sequence, even at least 10, 20, 30, 40, or even at least 50 templates of distinct sequence, and may be appended to 100, 500, 1000, even 5000 or more templates of distinct sequence.

In the first step, each of the plurality of templates of distinct sequence and a respective first oligonucleotide are concurrently annealed to a respective one of a plurality of probes within a single reaction mixture.

As in the uniplex embodiments described above, each probe includes at least a first region of complementarity to a respective one of the templates and at least a first oligo positioning region directly adjacent thereto. Also as in the uniplex embodiments described above, the nucleotide of the template complementarity region and the nucleotide of the oligo positioning region that are directly adjacent within the probe are said to be first junctional nucleotides that define a first probe junction therebetween.

Each first oligonucleotide includes a terminal region that is complementary to the first oligo positioning region of a respective probe. The terminal nucleotide of this oligonucleotide terminal region anneals to the first junctional nucleotide of the probe's first oligo positioning region.

A first ligatable free end is then created at the nucleotide of each of the plurality of templates that is annealed to the junctional nucleotide of its respective probe's first template complementarity region. As in the uniplex embodiments, the ligatable free end may readily be created using exonucleases; in embodiments in which template complementarity to probe is continuous, ligatable free ends may also readily be created using single strand-specific endonucleases.

In some embodiments, the sequence of the first oligonucleotide positioning region is identical among all of the plurality of probes. In such embodiments, a single species of first oligonucleotide may be used, thus appending identical oligonucleotides, and thus identical priming sites, to each of the plurality of templates.

In other embodiments, the sequence of the first oligonucleotide positioning region differs among the plurality of probes, and a different species of first oligonucleotide is appended to each of the plurality of templates of distinct sequence. Even in such embodiments, however, the plurality of first oligonucleotides may include a priming site that is identical thereamong. The priming site in such cases is typically positioned in optional oligonucleotide region 24. As in the uniplex embodiments of the methods of the present invention, the multiplex embodiments may be iterated to attach additional oligonucleotides to each of a plurality of templates of distinct sequence in one or more additional reactions.

In alternative embodiments, each of the plurality of probes further includes a second oligo positioning region directly adjacent to its template complementarity region. Template, respective first oligonucleotide, and respective second oligonucleotide are concurrently annealed to a respective one of a plurality of probes, followed by creation of first and second ligatable free ends and subsequent ligation.

Each first oligonucleotide may usefully include a first priming site that is common thereamong, and each second oligonucleotide may usefully include a second priming site that is common thereamong. In such embodiments, subsequent amplification of each of the templates of distinct sequence may be effected using common first and second primers. When the first and second priming sequences are reverse complements of one another, bidirectional amplification may be effected using a single common primer.

The multiplex methods of the present invention may include the further steps of separating the plurality of templates from the plurality of probes and oligonucleotides, and then amplifying the plurality of templates in a common reaction.

In multiplex embodiments of the methods of the present invention, the first and/or second oligonucleotide may usefully include a genotypic label ("bar code tag") that permits the separate identification of each unique template or product amplified therefrom.

Bar code tags are short nucleic acids having sequence that is designed algorithmically to maximize discrimination on a microarray displaying complements of the respective tags; a 1:1 correspondence as between tag sequence and nucleic acid to which it is appended permits each such nucleic acid to be identified by detection of the bar code uniquely associated therewith. See, e.g., Shoemaker et al., *Nature Genet.* 14(4):450–6 (1996); EP 0799897; Fan et al., *Genome Res.* 10:853–60 (2000); and U.S. Pat. No. 6,150,516, the disclosures of which are incorporated herein by reference in their entireties.

In the methods of the present invention, a distinct bar code sequence may be included in each species of first and/or each species of second oligonucleotide. In these embodiments, the terminal region of each species of oligonucleotide is distinct in sequence, and can anneal only to a single species of probe. The 1:1 correspondence as between tag sequence and template-appended oligonucleotide thus permits each template or product amplified therefrom to be identified by detection of the bar code uniquely associated therewith.

In other embodiments, bar codes may be appended to template 10 independently from oligonucleotides 20.

Figure 5A:
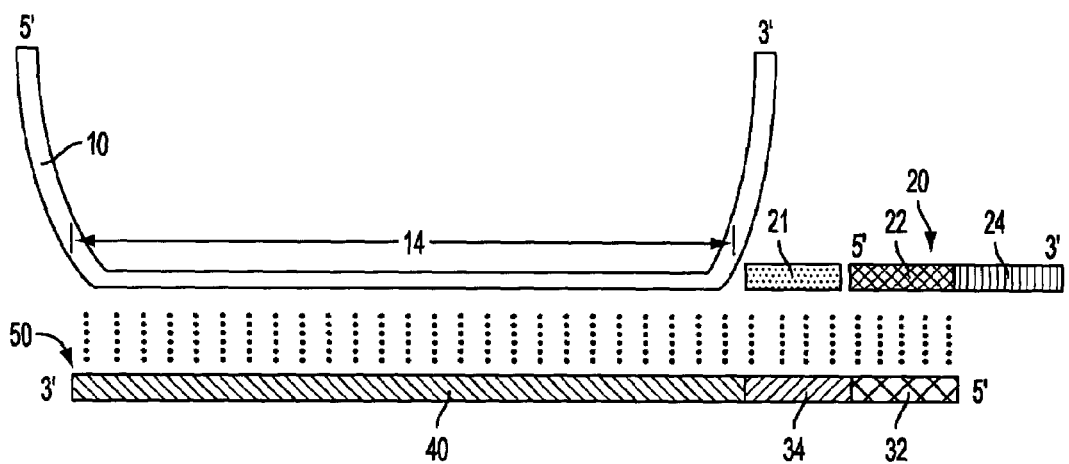
FIG. 5 is a schematic representation illustrating embodiments in which a plurality of oligonucleotides are appended in series to a single ligatable free end of the template, according to the present invention.
Figure 5B:
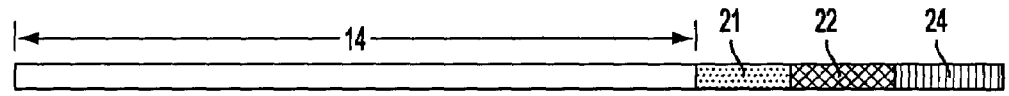

FIG. 5 schematizes embodiments of the present invention in which a plurality of oligonucleotides are appended in series to a single ligatable free end of template 10.

In these embodiments, probe 50 first oligo positioning region, referred to as 30 in previous figures, comprises at least subregions 34 and 32: oligo positioning subregion 32 is complementary to oligonucleotide 20 terminal region 22; subregion 34 is complementary to oligonucleotide 21.

In the first step of the method, template 10 and at least oligonucleotide 21 are annealed concurrently to probe 50. Typically, oligonucleotide 20 is also concurrently annealed to the probe. If not present, a ligatable free end is created on template 10, and template 10 is then ligated to oligonucleotide 21. Oligonucleotide 20 is ligated in series to oligonucleotide 21, either in a separate reaction or concurrently with ligation of oligonucleotide 21 to template 10.

Although shown as appended to a free 3' end of template 10, oligonucleotides 21 and 20 may be appended to a free 5' end of template 10.

In these embodiments, oligonucleotide 21 may include a bar code, thus permitting the bar code to be appended to the template independently of oligonucleotide 20, which optionally (but typically), includes a priming site.

When bar codes are appended to each of a 5' and 3' free end of template 10, the two bar codes uniquely associated with each template can be reverse complements of one another or different in sequence from one another.

Appending common first and second priming sites directly to each of the plurality of templates of distinct sequence—without prior amplification of the template— facilitates the subsequent stoichiometric amplification of a wide variety of templates of distinct sequence, obviating the problems of unequal amplification observed with many multiplex PCR approaches. By permitting the de novo design of the priming sites, independently of considerations of template sequence, the methods of the present invention also permit amplification with primers having optimal hybridization characteristics, decreasing artifacts such as primer dimer formation.

The following Examples are offered by way of illustration only, and not by way of limitation.

EXAMPLE 1

Oligonucleotide Attachment to Free Template Ends

A single probe is generated by amplifying DNA from a clone containing exon 14 of the cadherin gene, using dUTP instead of dTTP in the PCR reaction and primers complementary to vector sequences flanking the clone. PCR product consisting of exon 14 of the cadherin gene is used as template. Oligonucleotides are chemically synthesized.

In parallel reactions using serial dilutions of template ranging from 30 zmole to 30 fmole, template and a sufficient quantity of two different oligonucleotide species are concurrently hybridized to probe. Ligation is then performed using Taq ligase to append the common oligonucleotides to the annealed template.

UDG treatment is used to eliminate the probe, and a PCR reaction using common primers—one being the same as the oligonucleotide used in the preceding hybridization and ligation, the other being complementary to the oligo used in the hybridization and ligation—is performed.

Figure 6:
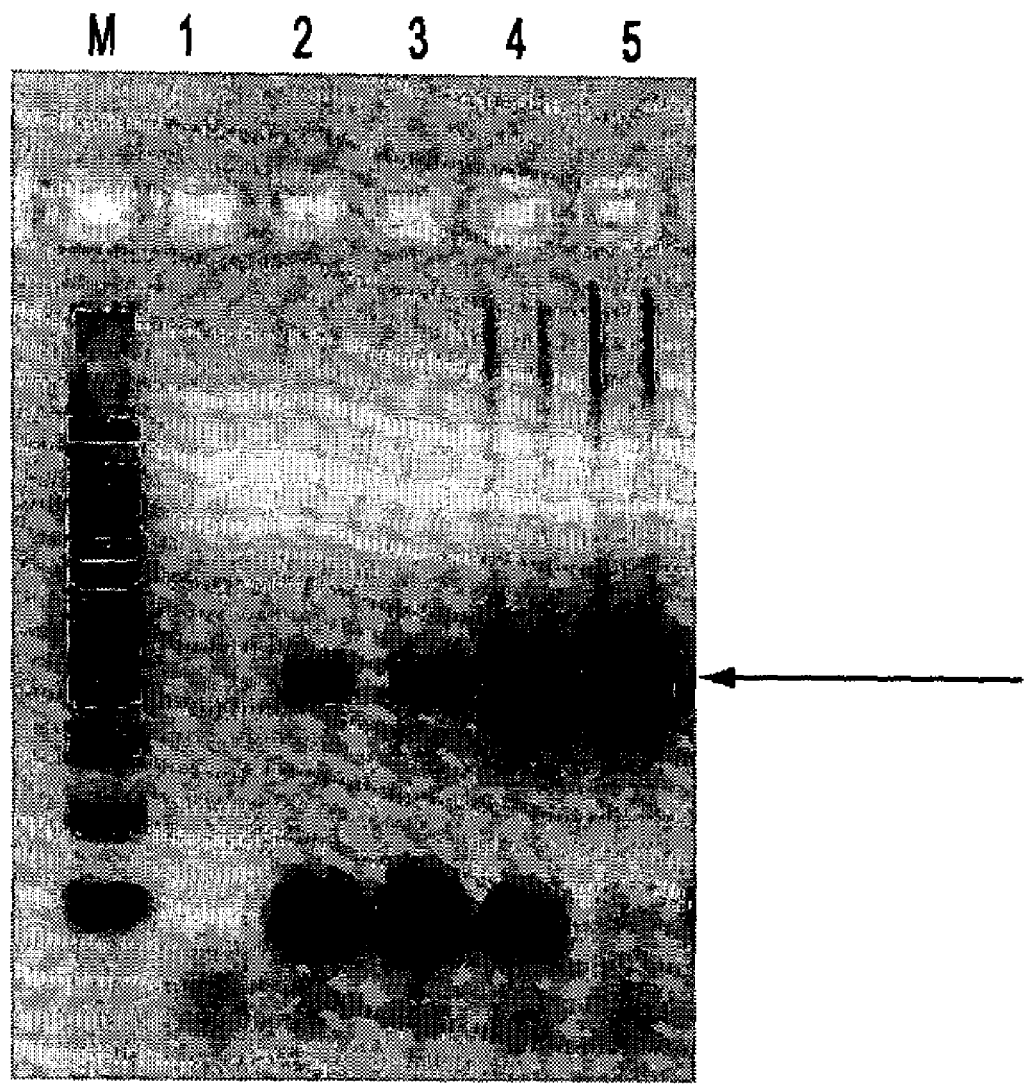
FIG. 6 is a photomicrograph of a gel showing amplification of as little as 30 zmole of template following oligonucleotide ligation.

FIG. 6 shows the results of the final PCR reaction, with lane 1 being a control lacking template, lane 2 showing results from 30 zmole of template, lane 3 showing results from 3 amole of template, lane 4 showing results from 0.3 fmole of template, and lane 5 showing results from 30 fmole of template.

As demonstrated in lane 2 in FIG. 6, as little as 30 zmole of initial template PCR is "captured" by probe-directed ligation of oligonucleotide, and amplified, with the migration of the amplified product indicated by an arrow. Increasing amounts of template in the hybridization and ligation results in increasing amounts of final amplified product as demonstrated in lanes 3, 4 and 5.

When no template is present for the initial hybridization and ligation reactions, no amplified product is detected, as demonstrated in lane 1. Additional controls, such as omitting hybridization oligonucleotides or probes, also result in the absence of amplified products (not shown).

The experimental conditions used are generally similar to those described in detail in Example 7, below.

EXAMPLE 2

Amplifying and Detecting a Plurality of Templates

Ten (10) probes are generated from 10 different clones.

Nine (9) templates are generated by PCR in an art-standard multiplex reaction using nine separate pairs of primers. Six of the templates perfectly match six (6) of the probes; two (2) probes have no matching template; one template has no matching probe; and two (2) templates match probes but the templates are a few nucleotides longer than the respective probe, precluding probe-directed positioning of oligonucleotides and ligation of oligonucleotides to the template.

Figure 7A:
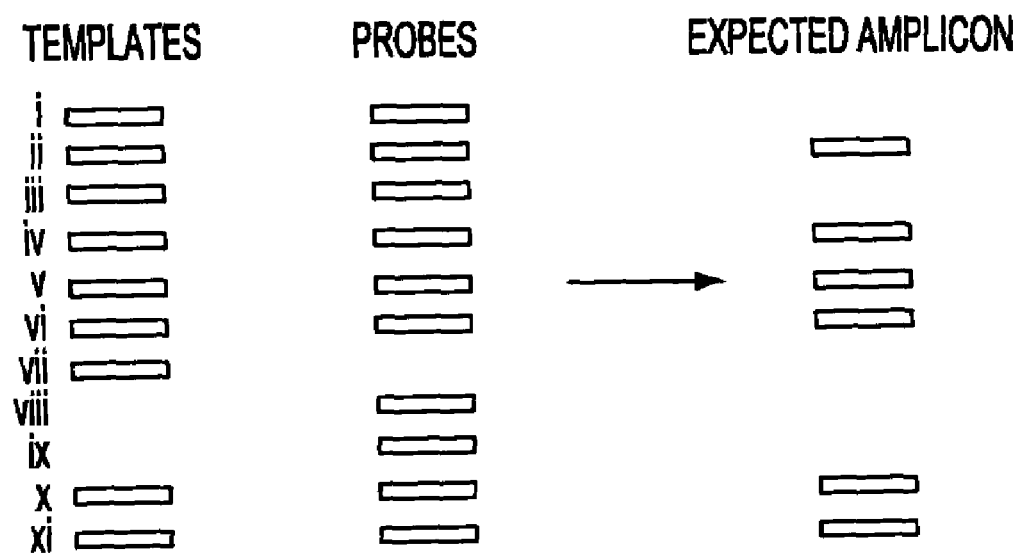
FIG. 7A is a schematic representation of the products expected from a series of probes and representative templates in a multiplexed reaction.

Therefore, only 6 fragments are expected after "capture" (i.e., probe-directed attachment of oligonucleotides to template) and amplification, as illustrated in FIG. 7A: fragments (ii), (iv), (v), (vi), (x) and (xi) are in both the template mixture and the probes; fragments (i) and (iii) are also present in both in the template mixture and the probes, but the templates include extra bases; fragment (vii) is in the template but not the probe; and fragments (viii) and (ix) are in the probe but not the template mixture.

Figure 7B:
FIG. 7B is a photomicrograph of a gel electrophoresis experiment showing the products actually obtained.

Pooled templates are hybridized to the pool of probes and oligonucleotides, followed by ligation, UDG treatment to eliminate the probe, and PCR amplification using common primers. The six expected fragments are recovered as shown in FIG. 7B, demonstrating the multiplexability and specificity of the procedure.

The experimental conditions used are generally similar to those described in Example 7 below.

EXAMPLE 3

Normalization of Template Dynamic Range

In these experiments, we expect that the various templates are present in widely different amounts, an artifact of the art-standard multiplex PCR reaction used to generate the templates. By utilizing a limiting amount of probe, however, we demonstrate here a decrease in the dynamic range of the ultimate product amplified by the common primers.

The 10 probes used in the preceding example (schematized in FIG. 7A) are used in this experiment at a concentration of 15 amole each. Ten (10) templates are used. The templates include the 9 templates shown in FIG. 7A as well as probe (viii) in FIG. 7A. Similar results are obtained whether the template is at 1.5 amole or 150 amole, with all products amplifying well, as demonstrated in FIG. 8.

Figure 8:
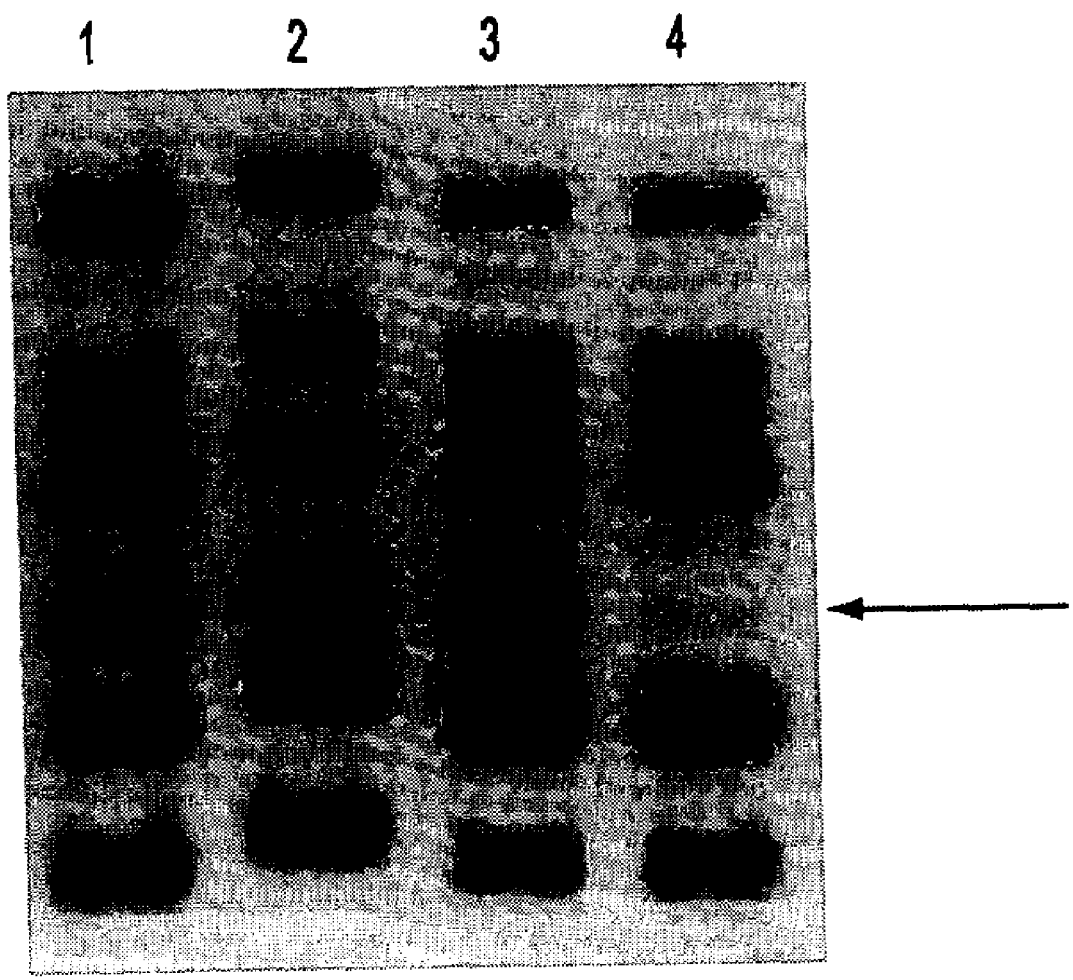
FIG. 8 is a photomicrograph of a gel electrophoresis experiment performed according to the present invention, showing products recovered from a complex mixture.

FIG. 8 shows the results of the PCR reaction with common primers following probe-directed oligonucleotide ligation to each of the templates.

In lane 1, all the templates are at 150 amole for the hybridization and ligation reaction. In lane 2, all the templates are at 1.5 amole. In lanes 3 and 4, all the templates are at 15 fmole except the template indicated by the arrow, which is at 150 and 1.5 amole respectively.

A difference of 10,000 fold in initial concentration, between 1.5 amole and 15 fmole, is thus reduced to approximately a 10-fold difference in the final product obtained. Without intending to be bound by theory, this normalization occurs because a limiting amount of probe (15 amole) is used.

The experimental conditions used are generally similar to those described in Example 7 below.

EXAMPLE 4

Detection of Templates from a Complex Mixture 135 pairs of primers are used to generate a complex PCR product, which serves as the template mixture. Templates include the 9 generated above in Example 2 as well as 126 unrelated templates. The same 10 probes described in Example 2 above are used to "capture" (i.e., to direct oligonucleotide addition to) the appropriate templates in the mixture using the same protocol outlined in Example 1 above. The experimental conditions used are generally similar to those described in Example 7 below.

Figure 9:
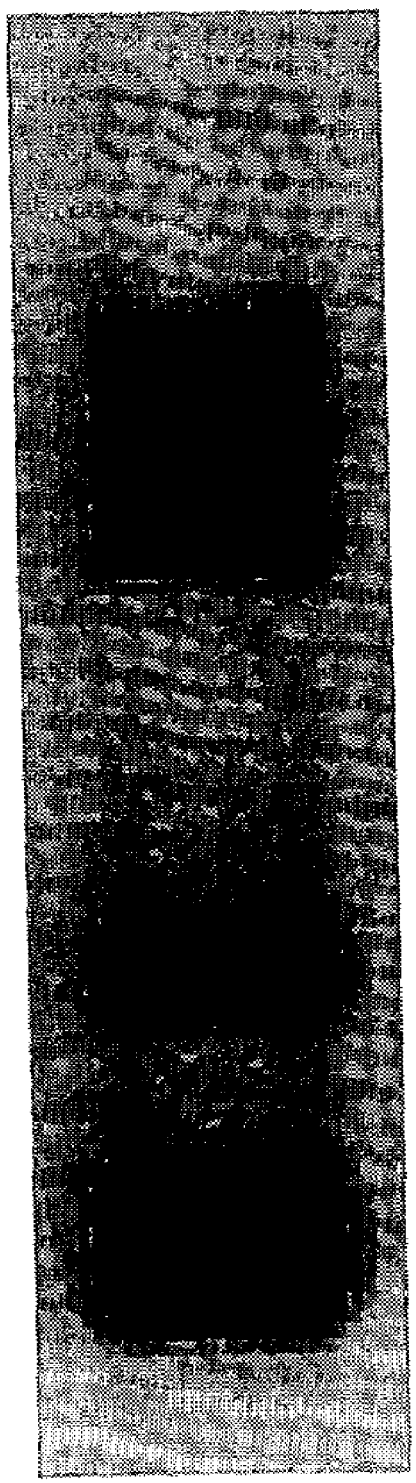
FIG. 9 is a photomicrograph of a gel electrophoresis experiment performed according to the present invention, showing products recovered from a complex mixture.

As shown in FIG. 9, all expected 6 fragments are recovered with a dynamic range no more than one order of magnitude.

EXAMPLE 5

Detection of 93 Templates in a Complex Mixture

A pool of 93 primer pairs are used to generate a template mixture and a corresponding 93 probes are utilized to direct oligonucleotide addition ("capture") using essentially the same protocol as described above.

Each primer pair has a 20 mer bar code sequence on one of the two paired primers, appending a unique bar code to each template before oligonucleotide addition. The bar code sequences are used to quantify the various amplicons.

After probe-directed oligonucleotide addition ("template capture") and amplification using the common primers, the amplified product is fluorescently labeled and hybridized to an array having oligonucleotide probes complementary to the bar code sequences.

Using this analysis, all 93 bar codes can be detected as indicators for their associated template amplicons.

While it is unlikely, given the specificity of the procedure demonstrated above, that some spurious product connected to a bar code is amplified after capture and amplification, the rigor with which the bar code tracks the desired amplicon is nevertheless confirmed as follows: the product amplified using the common primers is used as a template for another round of PCR using a bar code primer on one side and common primer on the other. In all 6 cases tested, a single band with the expected size is amplified, confirming the absence of spurious barcode-containing amplification products.

To confirm that the amplified sequence is that of the template and not the probe, the material amplified using the common primers is used as a template for PCR reactions to amplify specific fragments known to carry a single base variation between the template and the probe. Dideoxy sequencing is performed on the amplified products, and it is confirmed in all of the 4 test cases that the amplified products originate from the template.

The amount of each amplicon cannot be determined simply by the signal intensity of the various bar codes on the bar code array, because of the differential hybridization of various bar codes to their complements on the array. To control for such unequal hybridization, two color hybridization is used. Equimolar amounts of each amplicon are analyzed in one channel, and the specific amplified sample in the second channel. Analyzing the ratio of the two signals for each amplicon provides the amount of every fragment in the amplified sample.

Figure 10:
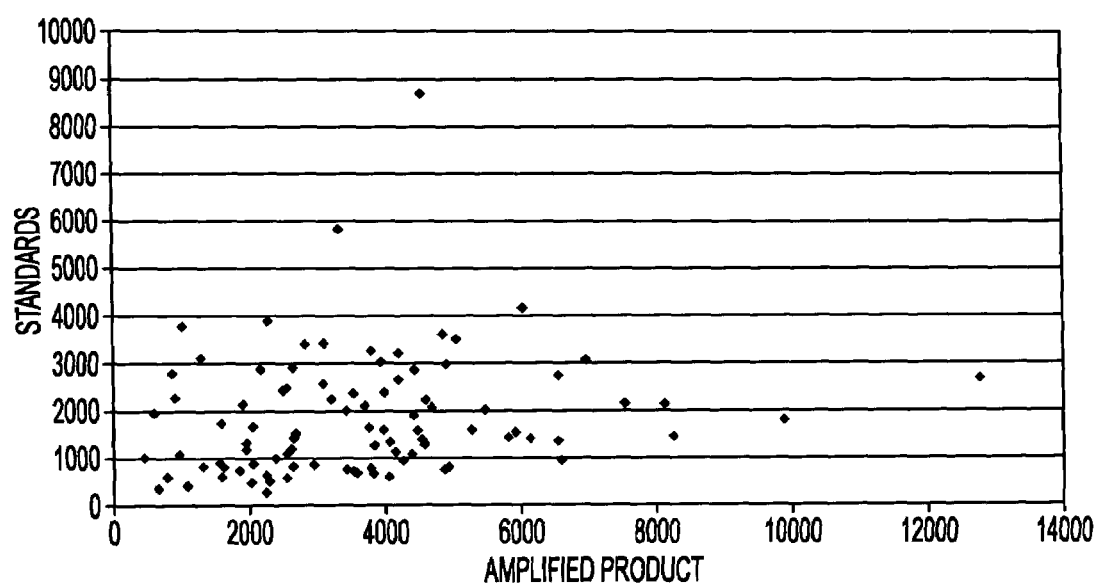
FIG. 10 is a graph plotting the hybridization signal of standard equimolar samples against the hybridization signal from an experimental sample.

As a measure of accuracy of quantification, the equimolar sample is tested by hybridizing in both channels. All 93 fragments are within a 2-fold range. Almost 97% of the amplified products are within a 20 fold range—a range at least as tight as that found with individual singleplex PCR (FIG. 10). This tight dynamic range is probably due to the use of a limiting amount of probe (1–10 amole), allowing for normalization of a large dynamic range in the template.

FIG. 10 shows the chip hybridization signal obtained for the various bar codes. The y axis shows the signal from the equimolar sample. The x axis shows the signal from our experimental sample, with the difference in the signals reflecting the differential hybridization and quantity of the bar codes. The ratio of these signals determines the amount of the various products.

The experimental conditions used are generally similar to those described in Example 7 below.

EXAMPLE 6

Independent Probe Hybridization to Template and Barcode

Barcodes are useful for the detection of different amplicons in a variety of applications. In Example 5 above, the barcode used is part of the primer in the initial template generation. In some applications it may not be desirable or possible to have the template prior-linked to the barcode, however. This is true, for example, when genomic DNA or cDNA serve as templates and oligonucleotides having primer sites are appended to sites internal to the template.

In one approach, the regions of complementarity within the probe direct the hybridization of both the template and the proper barcode. In addition to the extra hybridization event, an extra nick closure is necessary to generate a template to be amplified by common primers.

A pool of 69 probes carrying the desired template amplicons and barcodes are used. Template is generated using a pool of 36 primer pairs. Probes, templates, a pool of 69 oligonucleotides corresponding to the 69 barcodes, and the two common hybridization oligos are combined in the hybridization mix. Following hybridization, ligation, UDG treatment, and amplification using the common primers, the amount of the amplified fragments is determined using the same procedure as described above, i.e., two color hybridization.

The 36 barcodes with corresponding templates are detected to almost the same efficiency as when the barcode is appended during template generation. None of 33 barcodes lacking corresponding template is detected in the final amplified sample, confirming the authenticity of the barcode hybridization.

The experimental conditions used are generally similar to those described in Example 7 below.

EXAMPLE 7

Detection of More Than 1000 Templates in a Complex Mixture

Using 1180 clones, 1180 dUTP-containing probes are generated by amplification using vector primers. These probes are pooled and used to detect templates as described briefly above and in greater detail below.

For template generation, 1250 primer pairs are used in 13 different groups of 96 pairs each. Out of the 1250 products, 1180 are shown to have associated probes. The templates are pooled and hybridized to the probes and to 1250 barcode oligonucleotides in the same manner as described for the Example 6 above. Ligation is followed by UDG treatment and PCR with common primers.

The products are analyzed on the barcode chip using two color hybridization as described above. 85% of the products are within a 20 fold dynamic range. The majority of the failures are overlapping fragments from a specific 100 Kb region of the genome (at megabase 175 of human chromosome 2) ("MB175"). Excluding that region, about 94% of the products are within a 20 fold range.

The failures of amplification for the MB175 amplicons are shown to be due to failure in template generation, since "capture" of a pool of singleplex ("uniplex") PCR-generated products is successful. Template generation for these amplicons is demonstrated to be more successful if they are maintained as a separate group in the template generation step. This is probably because fragments with lower amplification efficiency are outcompeted by the higher efficiency amplification fragments during the template generation.

In general, where template generation is 96-plex or higher, followed by detection and amplification in 1000-plex or higher, separately generating templates for regions exhibiting low amplification efficiency may be preferred. Also, primer pairs for amplicons that failed are pooled together in order to get a higher success in template generation.

In one series of such 96-plex experiments, a first hybridization step is performed as before, but without addition of common oligonucleotides. After hybridization, Taq polymerase is added to extend the template using the probe as a template, resulting in the synthesis of one of the common priming sites. This is followed by a second hybridization step with the other common oligonucleotide, ligation, UDG-treatment to remove probe, and PCR with the both common oligonucleotides as described above.

The products are analyzed by chip as described above. The percentage of fragments in a 20 fold range is 77%, only slightly lower than for the two sided ligation method (80%). The reason for the lower recovery in this 96-plex as compared with results described above is likely that this particular panel had many of the fragments from the difficult to amplify MB175 region mentioned above.

Experimental protocols used are as follows:

1. Uracil-Containing Probe Generation by PCR

Plasmids containing inserts constructed and purified by Qiagen kit were used as a template to generate uracil-containing probes by PCR in 30μl reactions. Plasmids of about 3 fmol/μl (usually within the range of 1 to 10 fmol/μl) were diluted 100,000 times in TE to obtain 30 zmol/μl. PCR reactions were assembled on ice, using 1.5 μl diluted plasmids, 200 μM each of DATP, dCTP, dGTP (Amersham Biosciences, Piscataway, N.J.), 400 μM of dUTP (Applied Biosystems, Foster City, Calif.), 0.5 μM each of uracil-containing common forward primer (STF-U: 5'-GAC UUU AAA GUA AAA CGA CGG CCA-3' (SEQ ID No: 1)), reverse primer (STR-U: 5'-AGA UCU CUC GAG UGA UCA CC-3' (SEQ ID No: 2)), and 1.5 units of Taq DNA polymerase (NEB). The reactions were amplified in the GeneAmp™ 9700 thermocycler (Applied Biosystems, Foster City, Calif.) with pre-denaturation at 94° C. for 3 min, 32 cycles of 94° C. for 30 sec, 60° C. for 1 min and 72° C. for 1 min; final extension of 7 min. The PCR products were analyzed using 2% ethidium bromide-containing agarose gels and quantified using ImageQuant™ 5.2 (Molecular Dynamics/Amersham Biosciences, Sunnyvale, Calif.) after taking photomicrographs using a Kodak Image system. Generally, 95% of the reactions gave rise to the desired single product band. When there was no amplification, either performing PCR again or preparing new plasmids and then performing PCR again usually resulted in successful amplification.

The uracil-containing PCR products were pooled together in equal amounts to generate the probe pool (up to 1180 probes) for multiplex amplification. The probe pool was purified by Qiaquick® PCR purification kit (Qiagen) and eluted in 10 mM Tris-HCl, pH 8.0. For each of the later capture/hybridization reactions, 2 to 10 amol/probes were used in 20 or 30 μl to ensure that less than a few molecules of each of the original plasmids was present in the reaction.

2. Phosphorylation of Forward Primers and Bar Codes

The forward primers and oligo bar codes were phosphorylated by T4 polynucleotide kinase (T4 PNK, NEB). The pooled forward primers and oligo bar codes (each pool containing 96 oligos) were incubated at 37° C. for 60 min in 1× T4 DNA ligase buffer 50 mM Tris-Cl, pH 7.5, 10 mM MgCl2, 10 mM dithiothreitol, 1 mM ATP, 25 ug/ml bovine serum albumin) and 50 units of T4 PNK in 100 μl volume at 200 nM and 100 nM for each oligo, followed by 65° C. at 20 min to inactivate the PNK.

3. Template Generation by PCR Multiplexing:

Up to 96 primer pairs (forward and corresponding reverse primers) are used simultaneously to amplify many different loci to generate templates. DNA polymerases with high fidelity such as Pfu (proof-reading enzymes) were used with the corresponding buffers to ensure a low error rate for the amplification. The PCR reactions were done in 15 μl with 1× PfuTurbo® or PfuUltra™ PCR buffer (Stratagene), 30 ng human genomic DNA, 50 nM phosphorylated forward primer pool (each primer), 50 nM reverse primer pool, 200 μpM each of dNTP, additional 0.01% purified BSA (NEB), and 0.6 units of PfuTurbo® or PfuUltra™ (Stratagene). The final Mg2+ concentration was 4.5 mM-6.5 mM. The PCR was run at 95° C. for 2 min, followed by 7 cycles of 95° C. for 25 sec, 64° C. for 5 min with 1° C. decreases at each cycle and 72° C. for 3 min. This is followed by another 18 cycles of 95° C. for 25 sec, 57° C. for 5 min, and 72° C. for 3 min. The product was extended finally for 7 min at 72° C.

After PCR, the products were pooled for the same genomic DNA but with different primer pools, e.g., 13 wells to 1 well to obtain over 1000 amplicons for each well. 10 μl aliquots from each pooled well was run in a 2% agarose gel.

The pooled templates (PCR products) were further purified by Qiaquick® PCR purification system (Qiagen) or QuickStep™ 2 PCR purification system (Edge Biosystems) according to manufacturer's instructions. The purified templates were directly used for hybridization or dried up by Speedvac to allow more templates in the hybridization/capture reaction.

4. Hybridization/Capture

The hybridization was performed in 20 μl or 30 μl of final volume. For each 30 μl reaction, 100 fmol of each of two common flanking oligos (LTF: 5'-GAC TTT AAA GTA AAA CGA CGG CCA GTT CTT CCC -3' (SEQ ID No: 3); and LTRrevP: 5'-[phosp]CGC GCC CCG CGG TGA TCA CTC GAG AGA TCT -3' (SEQ ID No: 4)), 10 fmol of each corresponding bar code oligo, 5 amol of each corresponding uracil-containing probe, and the desired templates were combined in final 13 μl 0.3× SSPE. The mixture was heated to 94° C. for 2 min and quickly placed on ice-water for cooling. Then 17 μl of ice-cold SSPE/polyethylene glycol 8000 (mixture of 7 μl 20× SSPE+10 μl 30% PEG 8000) were added. The resulting hybridization mixture was placed on a heat block that had been pre-heated to over 80° C. The mixture was then subjected to 95° C. for 1 min, 70° C. for 20 min, 65° C. for 20 min, 60° C. for 20 min, 55° C. for 10 min, 50° C. for 10 min, and then held at 4° C.

After hybridization, the mixture was purified using the QuickStep™ 2 PCR purification system of Edge Biosystems according to manufacturer's instruction, except that 700×g for 2 min was used in the last spin. Due to the presence of PEG 8000, about twice the volume of original sample was obtained.

5. Ligation

The ligation was performed at 50° C. for 30 min followed by 55° C. for 20 min in a 40 μl volume, with 35 μl purified hybridization mix, 40 units of Taq DNA ligase (NEB) in 1×Taq ligase buffer (20 mM Tris-HCl, pH 7.6 at 25° C., 25 mM potassium acetate, 10 mM magnesium acetate, 10 mM DTT, 1 mM NAD and 0.1% Triton X-100).

6. Uracil-DNA Glycosylase (UDG) Treatment

To the above ligated product, 1 μl of UDG (1 unit, NEB) was added, and the mixture was incubated at 37° C. for 50 min, 94° C. for 3 min and then held at 4° C. The resulting UDG-treated ligation products can be used directly in next round PCR, with an appropriate adjustment of the Mg2+ contribution from ligase buffer.

7. Multiplex PCR for Template Detection and Amplification

PCR performed here amplifies the ligated products with a pair of common primers. Only the ligated products are amplified. The UDG-treatment ensure no amplification of uracil-containing probes.

Typically, the PCR was done in a 80 ul volume, with 20 μl UDG-treated ligation product, 200 μM each of dNTP, 0.5 μM each of forward primer (STF2P, phosphorylated: 5'-[phosp] GAC TTT AAA GTA AAA CGA CGG CCA-3' (SEQ ID 5) and reverse primer (STR: 5'-AGA TCT CTC GAG TGA TCA CC-3' (SEQ ID 6), 0.01% or 0.02% BSA, 2 mM Mg Mg2+, 3 units of PfuUltra DNA polymerase in 1× PfuUltra buffer. The reactions were amplified 25 cycles (95° C. for 2 min, 95° C. for 30 sec, 60° C. for 1 min, 72° C. for 5 min, and final extension of 72° C. for 7 min) in PE 9700. The PCR products were examined in a 2% agarose gel.

8. Chip Labeling

To examine the relative amount of the products in above PCR multiplexing reaction (up to 1180-plex), Genflex™ barcode chips (Affymetrix) were used. Two-color labeling was used with equimolar uracil probe labeled with biotin and the multiplex template detection stage("second stage") PCR product labeled with carboxyfluorescein (FAM). The extent of amplification of each product is obtained from the ratio of FAM signal over biotin signal (detected by a streptavidin-phycoerythrin fluorescent label), since equal amounts of probe are used on the chip.

To prepare for the chip labeling, 20 μl of the second stage PCR products were first treated with 50 units of Dra I (NEB) (cutting between the barcode and the rest of the amplicon), 10 units of exonuclease I (Exo I, USB) in total 40 μl of volume at 37° C. for 60 min, followed by denaturation at 80° C. for 30 min. The 10×PCR buffer with Mg2+ from Applied Biosystems (Foster City) was used to adjust the reaction buffer to 1×PCR buffer concentration. This step will generate short DNA fragments of less than 50 bp containing the bar code sequence, while eliminating single stranded short primers used in the second stage PCR reaction.

Using 40 μl of Dra I/Exo I-treated PCR products from the second stage PCR reaction as templates, linear amplification was done using a FAM- or biotin-labeled primer that has the same sequence as the common oligo sequence next to the bar code sequence (5'-A GTA AAA CGA CGG CCA GTdU CdUT[FAM] CCC-3' (SEQ ID 7) or 5'-A GTA AAA CGA CGG CCA GTdU CdUT[biotin] CCC -3' (SEQ ID 8)). The reaction was done in 50 μl containing a final dNTP concentration of 45 μM, 1.7 units of AmpliTaq Gold® DNA polymerase (Applied Biosystems, Foster City) and 1 μM of one of above labeled primer (95° C. for 5 min, 40 cycles of 95° C. for 30 sec, 58° C. for 1 min and 72° C. for 30 sec, final extension of 2 min).

After taking 5 ul of above reaction for later gel analysis, three microliter of UDG (3 units) were added to the rest of the reaction and further incubated at 37° C. for 20 min, followed by 96° C. for 10 min to generate a 24 mer labeled product containing a bar code.

Five microliters of samples before and after UDG treatment were separated in 10% precast, Ready Gel® urea-TBE PAGE gel (Bio-Rad) and the DNA fragments obtained after UDG were quantified to determine the total labeled products using the primer alone as standard.

For chip hybridization, a solution was prepared in 110 μl, containing 1×MES buffer, 1×Denhardt's Solution, 1.1 fmol each of GenFlex™ Tag Control, 1 fmol of each biotin-labeled product from probe and 5 fmol of each FAM-labeled product from PCR multiplexing. The mixture was denatured at 95° C. for 6 min, rapidly placed on ice-water for 2 min before loading to GenFlex chip pre-equilibrated in 1×MES buffer at room temperature. The hybridization was done overnight (12 to 16 hours) in an oven at 39° C. with rotation at about 19 rpm.

The chips were then washed sequentially with buffer A (6×SSPE, 0.0025% Tween 20) at room temperature, buffer B (2.25×SSPE, 0.0025% Tween 20) at 42° C., and filled with buffer A again in a Wash Station. They are stained with staining solution (6×SSPE, 1×Denhardt's Solution, 0.005% Tween 20 and 5 μg/ml streptavidin-phycoerythrin dye) for 10 min at room temperature with rotation of 25 rpm. The chips were washed again and filled with buffer A. The chips were scanned at both channels (530 nm and 570 nm) in a GeneArray Scanner (Agilent Technology, Palo Alto, Calif.). The data were analyzed, color separated to generate value for each channel. The ratio of FAM signal/biotin signal was used in later analysis.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention may be practiced by other than the described embodiments, which are presented for purposes of illustration only and not by way of limitation. The present invention is limited only by the claims that follow.

What is claimed is:

1. A method of appending at least a first oligonucleotide and a second oligonucleotide directly to a nucleic acid template, the method comprising:

concurrently annealing the template and at least a first oligonucleotide and a second oligonucleotide to at least a first probe, wherein said probe includes at least a first template complementarity region and at least a first oligo positioning region directly adjacent thereto, the nucleotide of the first template complementarity region and the nucleotide of the first oligo positioning region that are directly adjacent within said probe being first junctional nucleotides that define a first probe junction therebetween, and wherein said probe further includes a second oligo positioning region directly adjacent to said first template complementarity region, the nucleotide of the first template complementarity region and the nucleotide of the second oligo positioning region that are directly adjacent within said probe being second junctional nucleotides that define a second probe junction therebetween and wherein said first oligonucleotide includes a terminal region that is complementary to the first oligo positioning region of said probe, the terminal nucleotide of said terminal oligonucleotide region being annealed to the junctional nucleotide of the probe's first oligo positioning region;

and wherein said second oligonucleotide includes a terminal region that is complementary to the second oligo positioning region of said probe, the terminal nucleotide of said terminal oligonucleotide region being annealed to the junctional nucleotide of the second oligo positioning region;

creating a first ligatable free end at the template nucleotide that is annealed to the junctional nucleotide of the probe's first template complementarity region; and then ligating said first oligonucleotide to said template first free ligatable end to append said first oligonucleotide to the nucleic acid template; and creating a second ligatable free end at the template nucleotide that is annealed to the second junctional nucleotide of the first template complementarity region; and ligating said second oligonucleotide to said template second ligatable free end, and then separating said template from said probe and said oligonucleotides.

2. The method of claim 1, wherein said first ligatable free end and said second ligatable free end are created by removing template regions that are noncomplementary to said probe first complementarity region by exonucleolytic digestion.

3. The method of claim 2, wherein said template non-complementary regions are removed by digestion with Exonuclease VII or a combination of Exonuclease T and rec Jf.

4. The method of claim 1, wherein said first ligatable free end and said second ligatable free end are created by removing template regions that are noncomplementary to said probe first complementarity region by digestion with a single-strand specific endonuclease.

5. The method of claim 4, wherein said endonuclease is mung bean nuclease.

6. The method of claim 1, wherein said probe further comprises means for separating said probe from said template.

7. The method of claim 6, wherein said separating means are a plurality of incorporated deoxyuridine residues.

8. The method of claim 7, wherein said separating step comprises cleaving said probe at said deoxyuridine residues into a plurality of probe fragments, and then size separating said template from said probe fragments and from said oligonucleotides.

9. The method of claim 6, wherein said separating means are one or more capture moieties.

10. The method of claim 1, further comprising the step, after separating said template from said probe and said oligonucleotides, of: amplifying a region of said template between said first and second appended oligonucleotides and wherein at least one of said first and second oligonucleotides comprises a bar code sequence.

11. The method of claim 10, wherein said first oligonucleotide has a first priming site and said second oligonucleotide has a second priming site, and said amplifying is performed by priming polymerization at said first priming site and said second priming site.

12. The method of claim 11, wherein said template region is amplified by PCR.

13. The method of claim 1, wherein said template is derived from cDNA.

14. The method of claim 1, wherein said template is derived from genomic DNA.

15. The method of claim 14, wherein said genomic DNA is from a single individual.

16. The method of claim 14, wherein said genomic DNA is pooled from a plurality of individuals.

17. The method of claim 14, wherein said genomic DNA is derived from a eukaryote.

18. A method of appending at least a first oligonucleotide and a second oligonucleotide directly to each of a plurality of nucleic acid templates of distinct sequence in a single reaction, the method comprising:

concurrently annealing each template and a respective first oligonucleotide to a respective one of a plurality of probes within a single reaction mixture, wherein each probe includes at least a first region of complementarity to a respective one of said templates, at least a first oligo positioning region directly adjacent thereto, the nucleotide of the template complementarity region and the nucleotide of the first oligo positioning region that are directly adjacent within said probe being first junctional nucleotides that define a first probe junction therebetween, and a second oligo positioning region directly adjacent to the first template complementarity region, the nucleotide of the template complementarity region and the nucleotide of the second oligo positioning region that are directly adjacent within said probe being second junctional nucleotides that define a second probe junction therebetween, and wherein each said first oligonucleotides includes a priming sequence that is common thereamong and a terminal region that is complementary to the first oligo positioning region of a respective probe, the terminal nucleotide of said first oligonucleotide region being annealed to the first junctional nucleotide of the first oligo positioning region;

appending a second oligonucleotide to each of said plurality of templates of distinct sequence by: annealing a respective second oligonucleotide to each probe concurrently with annealing of said template to said probe, wherein said second oligonucleotide includes a terminal region that is complementary to the second oligo positioning region of its respective probe, the terminal nucleotide of said terminal oligonucleotide region being annealed to the junctional nucleotide of the second oligo positioning region;

creating a first ligatable free end at the nucleotide of each template that is annealed to the junctional nucleotide of its respective first template complementarity region;

creating a second ligatable free end at the template nucleotide that is annealed to the second junctional nucleotide of the first template complementarity region; and then ligating each said first oligonucleotide to its respective template first ligatable free end to append said first oligonucleotide to its respective template within said plurality of nucleic acid templates and ligating said second oligonucleotide to said second ligatable free end.

19. The method of claim 18, wherein each of said second oligonucleotides includes a priming sequence that is common thereamong.

20. The method of claim 19, further comprising the step, after ligating, of: separating said templates from said probes and said oligonucleotides.

21. The method of claim 20, further comprising the step, after separating said templates from said probes and said oligonucleotides, of: concurrently amplifying a region of each said template.

22. The method of claim 21, wherein said amplifying is performed by priming polymerization at said first common priming site and said second common priming site.

23. The method of claim 22, wherein said template region is amplified by PCR.

24. The method of claim 23, wherein said plurality includes at least 10 templates of distinct sequence.

25. The method of claim 24, wherein said plurality includes at least 100 templates of distinct sequence.

26. The method of claim 25, wherein said plurality includes at least 1000 templates of distinct sequence.

27. The method of claim 19, wherein at least one of said first and second oligonucleotides comprises a bar code sequence.

28. The method of claim 18, wherein each of said first ligatable free ends is created by removing template regions that are noncomplementary to said probe first complementarity region.

29. The method of claim 28, wherein said template noncomplementary regions are removed by exonucleolytic digestion.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence

```
<220> FEATURE:
<223> OTHER INFORMATION: Description of Artificial Sequence: Primer
<220> FEATURE:
<223> OTHER INFORMATION: Description of Combined DNA/RNA Molecule:
      Synthetic DNA/RNA sequence
<220> FEATURE:
<221> NAME/KEY: modified_base
<222> LOCATION: (4)..(6)
<223> OTHER INFORMATION: dU
<220> FEATURE:
<221> NAME/KEY: modified_base
<222> LOCATION: (11)
<223> OTHER INFORMATION: dU

<400> SEQUENCE: 1
gacuuuaaag uaaaacgacg gcca                                        24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Description of Combined DNA/RNA Molecule:
      Synthetic DNA/RNA sequence
<220> FEATURE:
<221> NAME/KEY: modified_base
<222> LOCATION: (4)
<223> OTHER INFORMATION: dU
<220> FEATURE:
<221> NAME/KEY: modified_base
<222> LOCATION: (6)
<223> OTHER INFORMATION: dU
<220> FEATURE:
<221> NAME/KEY: modified_base
<222> LOCATION: (8)
<223> OTHER INFORMATION: dU
<220> FEATURE:
<221> NAME/KEY: modified_base
<222> LOCATION: (13)
<223> OTHER INFORMATION: dU
<220> FEATURE:
<221> NAME/KEY: modified_base
<222> LOCATION: (16)
<223> OTHER INFORMATION: dU

<400> SEQUENCE: 2
agaucucucg agugaucacc                                             20

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gactttaaag taaaacgacg gccagttctt ccc                              33

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgcgccccgc ggtgatcact cgagagatct                                  30
```

```
<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: 5' phosphorylation

<400> SEQUENCE: 5
gactttaaag taaaacgacg gcca                                              24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
agatctctcg agtgatcacc                                                   20

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA/RNA sequence
<220> FEATURE:
<223> OTHER INFORMATION: Description of Combined DNA/RNA Molecule:
      Synthetic DNA/RNA sequence
<220> FEATURE:
<221> NAME/KEY: modified_base
<222> LOCATION: (19)
<223> OTHER INFORMATION: dU
<220> FEATURE:
<221> NAME/KEY: modified_base
<222> LOCATION: (21)
<223> OTHER INFORMATION: dU

<400> SEQUENCE: 7
agtaaaacga cggccagtuc utccc                                             25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA/RNA sequence
<220> FEATURE:
<223> OTHER INFORMATION: Description of Combined DNA/RNA Molecule:
      Synthetic DNA/RNA sequence
<220> FEATURE:
<221> NAME/KEY: modified_base
<222> LOCATION: (19)
<223> OTHER INFORMATION: dU
<220> FEATURE:
<221> NAME/KEY: modified_base
<222> LOCATION: (21)
<223> OTHER INFORMATION: dU

<400> SEQUENCE: 8
agtaaaacga cggccagtuc utccc                                             25
```